(12) United States Patent
Aizawa et al.

(10) Patent No.: US 10,955,413 B2
(45) Date of Patent: Mar. 23, 2021

(54) METHOD FOR MEASURING ZYGOMYCOTA AND REAGENT KIT FOR MEASURING ZYGOMYCOTA

(71) Applicant: SEIKAGAKU CORPORATION, Tokyo (JP)

(72) Inventors: Maki Aizawa, Tokyo (JP); Koichi Makimura, Tokyo (JP)

(73) Assignee: SEIKAGAKU CORPORATION, Tokyo (JP)

( * ) Notice: Subject to any disclaimer, the term of this patent is extended or adjusted under 35 U.S.C. 154(b) by 567 days.

(21) Appl. No.: 15/561,265

(22) PCT Filed: Mar. 25, 2016

(86) PCT No.: PCT/JP2016/059741
§ 371 (c)(1),
(2) Date: Sep. 25, 2017

(87) PCT Pub. No.: WO2016/153058
PCT Pub. Date: Sep. 29, 2016

(65) Prior Publication Data
US 2018/0120315 A1  May 3, 2018
US 2019/0154686 A2  May 23, 2019
US 2019/0339270 A2  Nov. 7, 2019

(30) Foreign Application Priority Data

Mar. 26, 2015 (JP) .............................. JP2015-063887

(51) Int. Cl.
*G01N 33/569* (2006.01)

(52) U.S. Cl.
CPC ... *G01N 33/56961* (2013.01); *G01N 2333/37* (2013.01); *G01N 2400/28* (2013.01)

(58) Field of Classification Search
None
See application file for complete search history.

(56) References Cited

U.S. PATENT DOCUMENTS

2013/0260395 A1  10/2013  Luppi et al.
2015/0309019 A1  10/2015  Kaneko et al.

FOREIGN PATENT DOCUMENTS

| JP | 2004-258024 A | 9/2004 |
| JP | 2006-518990 A | 8/2006 |
| JP | 2012-149896 A | 8/2012 |
| JP | 2014-200201 A | 10/2014 |
| WO | 2004/059280 A2 | 7/2004 |
| WO | 2014087802 A1 | 6/2014 |

OTHER PUBLICATIONS

Lass-Flörl, Zygomycosis: conventional laboratory diagnosis, Clin. Microbiol Infect., 15(suppl. 5), (2009), p. 60-65 (Year: 2009).*
Ibrahim and Kontoyiannis, Update on mucormycosis pathogensis, 26(6), (2013), p. 508-515 (Year: 2013).*
Wildlife Health Australia, "WHA Fact Sheet: Mucormycosis in the platypus." Web. Apr. 2006. (12 pages). https://www.wildlifehealthaustralia.com.au. Accessed on Apr. 23, 2020 (Year: 2006).*
Thorton et al., Development of an Immunochromatographic Lateral-Flow Device for Rapid Serodiagnosis of Invasive Aspergillosis, Clinical and Vaccine Immunology, 15(7), (2008), p. 1095-1105 (Year: 2008).*
Rafaat et al., Chitosan and its antimicrobial potential—a critical literature survey, Microbial Biotechnology, 2(2), (2009), p. 186-201 ( Year: 2009).*
International Preliminary Report on Patentability dated Oct. 5, 2017 in counterpart international application No. PCT/JP2016/059741, (13 pages).
Zamani et al., "Extraction and Precipitation of Chitosan from Cell Wall of Zygomycetes Fungi by Dilute Sulfuric Acid," Biomacromolecules, 2007, vol. 8, No. 12, pp. 3785-3790.
Sorlier et al., "Preparation and Development of Anti-Chitosan Antibodies," J. Biomed. Mater. Res. Pt. A, 2003, vol. 67A, No. 3, pp. 766-774.
International Search Report dated Jun. 21, 2016 issued in international application No. PCT/JP2016/059741, (5 pages).
Miyazaki et al., "Setsugokinsho no Kan'i Shindanho Kaihatsu ni Muketa Kogen Kensaku no Kenkyu," Medical Mycology Research Center, Chiba University Hokoku, 2013, vol. 16, p. 59, Kenkyu Kadai '11-06. (4 pages total).
Notification of Reason(s) for Refusal dated Jan. 14, 2020 from the Japanese Patent Office in application No. 2017-507643, (8 pages).
Partial Translation: Kawabata, "Setsugo Kinrui (Mucor) Dotei no Tameno Grocott Senshoku no Zenshori", Med. Technol., 2010, vol. 38, No. 12, pp. 1166-1168.
Partial Translation: Kikuchi, "Chitosan Kenshutsuyo Tanpakushitsu Probe no Kaihatsu to Shijokin no Saiboheki Kozo no Kaiseki eno Riyo," Annual Meeting of Union of Chemistry-Related Societies in Chuba Area, Japan Koen Yokoshu, 2013, p. 223, 2K18. (3 pages total).
Partial Translation: "Shin Seikagaku Jikken Koza 17 Biseibutsu Jikkenho," Tokyo Kagaku Dojin, 1992, Jikken Hoho, pp. 228-231. (3 pages total).
Communication dated Jul. 10, 2018, from the European Patent Office in counterpart European Application No. 16768961.1, (10 pages).

(Continued)

*Primary Examiner* — Ellen J Marcsisin
(74) *Attorney, Agent, or Firm* — Sughrue Mion, PLLC

(57) ABSTRACT

An object of the present invention is to provide means for correctly measuring zygomycota. The present inventors have found that conventionally difficult zygomycota measurement can be performed through subjecting an untreated specimen to an acid treatment. The present invention provides a method for measuring zygomycota, the method including measuring zygomycota in a specimen that was subjected to an acid treatment; an agent for preparing a specimen for measurement of zygomycota; a method for preparing a specimen for measurement of zygomycota; and a reagent kit for measuring zygomycota.

8 Claims, 1 Drawing Sheet

(56) References Cited

OTHER PUBLICATIONS

De Ruiter, et al., "Isolation and characterization of beta(1-4)-D-glucuronans from extracellular polysaccharides of moulds belonging to Mucorales", Jan. 1, 1992, pp. 1-7, vol. 18, No. 1, Carbohydrate Polymers, Applied Science Publishers, Ltd., Barking, GB, XP024147795 (7 pages total).

Lass-Flörl, "Zygomycosis: conventional laboratory diagnosis", Jan. 1, 2009, pp. 60-65, vol. 15, Clinical Microbiology and Infection., United Kingdom, Switzerland, XP055488986 (6 pages total).

Millon, et al., "Quantitative Polymerase Chain Reaction Detection of Circulating DNA in Serum for Early Diagnosis of Mucormycosis in Immunocompromised Patients", Feb. 18, 2013, pp. e95-e101, vol. 56, No. 10, Clinical Infectious Diseases, XP055488991 (7 pages total).

Schubert, et al., "A Monoclonal Antibody That Specifically Binds Chitosan In Vitro and In Situ on Fungal Cell Walls", Aug. 28, 2010, pp. 1179-1184, vol. 20, No. 8, Journal of Microbiology and Biotechnology, XP055488867 (6 pages total).

Kawabata, "Setsugo Kinrui (Mucor) Dotei no Tameno Grocott Senshoku no Zenshori," Med. Technol., 2010, vol. 38, No. 12, pp. 1166-1168.

Kikuchi, "Chitosan Kenshutsuyo Tanpakushitsu Probe no Kaihatsu to Shijokin no Saiboheki Kozo no Kaiseki eno Riyo," Annual Meeting of Union of Chemistry-Related Societies in Chuba Area, Japan Koen Yokoshu, 2013, p. 223, 2K18. (3 pages total).

"Shin Seikagaku Jikken Koza 17 Biseibutsu Jikkenho," Tokyo Kagaku Dojin, 1992, Jikken Hoho, pp. 228-231, 12,1,1b. (3 pages total).

\* cited by examiner

METHOD FOR MEASURING ZYGOMYCOTA AND REAGENT KIT FOR MEASURING ZYGOMYCOTA

CROSS REFERENCE TO RELATED APPLICATIONS

This application is a National Stage of International Application No. PCT/JP2016/059741, filed Mar. 25, 2016 (claiming priority based on Japanese Patent Application No. 2015-063887, filed Mar. 26, 2015), the contents of which are incorporated herein by reference in their entirety.

TECHNICAL FIELD

The present invention relates to means for measuring a specific fungus. More particularly, the present invention relates to a method for measuring zygomycota, an agent for preparing a specimen for measurement of zygomycota, a method for preparing a specimen for measurement of zygomycota, a reagent kit for measuring zygomycota, and the like.

BACKGROUND ART

Mycosis is defined as an infectious disease caused by fungi settled onto the skin, the organs, etc. of animals. Fungi collectively refer to living organisms belonging to the kingdom Fungi. Known types of mycosis include dermatomycosis (superficial mycosis), deep dermatomycosis (deep superficial mycosis), and deep-seated mycosis (systemic mycosis, visceral mycosis). Dermatomycosis is a type of mycosis localized on the skin, and known examples thereof include tinea alba, tinea versicolor, and skin candidosis. Deep dermatomycosis is a type of mycosis localized at the derma and subcutaneous tissue, and known examples thereof include sporotrichosis and entomophthoramycosis. Deep-seated mycosis is a type of mycosis localized at the organs, and examples thereof include aspergillosis, candidosis, cryptococcosis, and mucormycosis.

Among various types of mycosis, infectious diseases caused by Zygomycota are collectively called zygomycosis. Examples of zygomycosis include mucormycosis caused by zygomycota belonging to the subphylum Mucoromycotina, and entomophthoramycosis caused by zygomycota belonging to the subphylum Entomophthoromycotina.

In the cell wall of a fungus, chitosan and chitin are known to be present. More specifically, the cell walls of fungi belonging to the phylum Ascomycota, the phylum Basidiomycota, or the phylum Chytridiomycota contain chitin and (1→3)-β-D-glucan (hereinafter referred to simply as "β-glucan"), while the cell walls of fungi belonging to the phylum Zygomycota predominantly contain chitosan rather than chitin and substantially does not contain β-glucan.

Non-Patent Document 1 discloses that the number of cases of visceral mycosis (deep-seated mycosis) such as mucormycosis has been increasing, since an immunosuppressive therapy is widely conducted to cancers, blood diseases, etc. The document also discloses that mucormycosis is a fulminant mycosis with a death rate of about 60% of infected subjects, and that the rate of mucormycosis infection among total mycosis infections gradually increases. Further, the same document discloses that there is no serological diagnostic support for mucormycosis effective for an early diagnosis thereof, and this fact is increasingly problematic.

As described above, the present invention is related to means for measuring zygomycota. In this regards, Patent Document 1 discloses a microassay for saccharides such as chitosan by use of an anti-saccharide antibody, which can be used in high-sensitivity detection of a saccharide. However, Patent Document 1 is absolutely silent to a chitosan assay of biological samples by use of specific assay means.

Patent Document 2 discloses a method for detecting and identifying a fungus causing zygomycosis through PCR by use of a DNA fragment in a specimen as a template and a set of a sense primer and an anti-sense primer specific to the DNA fragment of the objective fungus causing zygomycosis. In the Examples of Patent Document 2, the specimen is pretreated with protease K.

PRIOR ART DOCUMENTS

Patent Documents

Patent Document 1: Japanese Patent Application Laid-Open (kokai) No. 1996-193100
Patent Document 2: Japanese Patent Application Laid-Open (kokai) No. 2014-200201

Non-Patent Documents

Non-Patent Document 1: Hisako KUSHIMA, Issei TOKIMATSU, and Junichi KADOTA, "Deep-Seated Mycosis Caused by Rare Fungi", The Journal of the Japanese Association For Infectious Diseases, Vol. 88, No. 4, p. 531-532

SUMMARY OF THE INVENTION

Problems to be Solved by the Invention

Currently, a certain antifungal agent which is effective for the therapy of mycosis including zygomycosis is provided. Under the circumstances, the present inventors have conducted extensive studies on means for measuring zygomycota which enables determination of possibility of administration of such an antifungal agent and confirmation of the efficacy of administration of the agent. As a result, when a blood-derived sample (e.g., a serum) is subjected to immunoassay as is, the zygomycota assay cannot be desirably realized with a level expected from the disclosure in Patent Document 1. This fact is clarified in the below-mentioned Examples.

An object of the present invention is to provide means for measuring zygomycota. Another object of the present invention is to provide, in one embodiment, means for realizing a serological diagnosis for zygomycosis such as mucormycosis or entomophthoramycosis, the means being effective for an early diagnosis thereof.

Means for Solving the Problems

In order to solve the aforementioned problems, the present inventors have conducted extensive studies on means for measuring zygomycota, more particularly, on the method for pretreating a specimen, the method enabling measurement of zygomycota. Generally, examples of conceivable methods for pretreating a specimen include addition of a surfactant, addition of an organic solvent, addition of a metal salt, addition of an enzyme (e.g., nuclease, protease, lipase, or glycosidase), suspending by means of ultrasonication, beads or the like, homogenization by means of a homogenizer or the like, column treatment, treatment with a filtration filter, and various other methods. However, surprisingly, the present inventors have found that measurement of zygomycota can be performed through treating a specimen under acidic conditions (i.e., acid treatment), the treatment being a considerably simple and inexpensive technique. The present invention has been accomplished on the basis of this finding.

The aforementioned problems can be solved by the present invention including the following embodiments.

[1]
A method for measuring zygomycota, the method comprising measuring zygomycota in a specimen that was subjected to an acid treatment.

[2]
The method according to [1] above, wherein the acid treatment is performed by coexisting an untreated specimen with an acid component.

[3]
The method according to [2] above, wherein the acid component is one or more of acids selected from the group consisting of an oxoacid, an organic acid, and an inorganic acid.

[4]
The method according to [3] above, wherein the oxoacid is one or more of acids selected from the group consisting of a carboxylic acid, a sulfonic acid, sulfuric acid, phosphoric acid, nitric acid, and a halogen oxoacid.

[5]
The method according to [3] above, wherein the organic acid is a carboxylic acid and/or a sulfonic acid.

[6]
The method according to [4] or [5] above, wherein the carboxylic acid is one or more of acids selected from the group consisting of acetic acid, formic acid, citric acid, and oxalic acid.

[7]
The method according to [3] above, wherein the inorganic acid is one or more of acids selected from the group consisting of a hydrogen halide, sulfuric acid, phosphoric acid, nitric acid, and a halogen oxoacid.

[8]
The method according to [7] above, wherein the hydrogen halide is hydrochloric acid.

[9]
The method according to [4] or [7] above, wherein the halogen oxoacid is a hypohalous acid and/or a perhalogenic acid.

[10]
The method according to [9] above, wherein the hypohalous acid is one or more of acids selected from the group consisting of hypochlorous acid, hypobromous acid, and hypoiodous acid.

[11]
The method according to [9] above, wherein the perhalogenic acid is one or more of acids selected from the group consisting of perchloric acid, perbromic acid, and periodic acid.

[12]
The method according to any one of [1] to [11] above, the method being performed using a reagent for detecting a component of zygomycota.

[13]
The method according to [12] above, wherein the reagent for detecting a component of zygomycota is an anti-chitosan antibody.

[14]
The method according to any one of [1] to [13] above, the method being performed by immunoassay.

[15]
The method according to [14] above, wherein the immunoassay is performed using an anti-chitosan antibody.

[16]
The method according to [14] or [15] above, wherein the immunoassay is enzyme-linked immunosorbent assay (ELISA), immunochromatography, immunoblotting, a flocculation method, turbidimetry, or nephelometry.

[17]
The method according to [16] above, wherein the flocculation method is latex flocculation method.

[18]
The method according to any one of [1] to [17] above, wherein the specimen is derived from an animal.

[19]
The method according to [18] above, wherein the animal-derived specimen is a blood-derived sample, bronchoalveolar lavage fluid (BALF), a biopsy specimen, sputum, cerebrospinal fluid, nasal swab, pharyngeal swab, nasal aspirate, or ascites.

[20]
The method according to [19] above, wherein the blood-derived sample is a serum or plasma.

[21]
The method according to any one of [1] to [20] above, the method being a method for detecting zygomycosis.

[22]
The method according to [21] above, wherein the zygomycosis is mucormycosis or entomophthoramycosis.

[23]
An agent for preparing a specimen for measurement of zygomycota, the agent containing an acid component.

[24]
The agent according to [23] above, the agent being used for the acid treatment of a specimen to be subjected to the method as recited in any one of [1] to [22] above.

[25]
An acid component for use in an acid treatment of a specimen to be subjected to measurement of zygomycota.

[26]
The acid component according to [25] above, the acid component being used for the acid treatment of a specimen to be subjected to the method as recited in any one of [1] to [22] above.

[27]
A method for preparing a specimen for measurement of zygomycota, the method comprising subjecting an untreated specimen to an acid treatment.

[28]
The method according to [27] above, wherein the acid treatment is carried out for preparing the specimen to be subjected to the method as recited in any one of [1] to [22] above.

[29]
The method according to [27] or [28] above, wherein the acid treatment is performed by coexisting an untreated specimen with an acid component.

[30]
The method according to [29] above, wherein the treatment of coexisting an untreated specimen with an acid component is a treatment of coexisting an untreated specimen with the agent as recited in [23] or [24] above.

[31]

A reagent kit for measuring zygomycota, the kit comprising a reagent containing an acid component and/or a reagent for detecting a component of zygomycota.

[32]

A reagent kit for use in the method as recited in any one of [1] to [22] above, the kit comprising a reagent containing an acid component and/or a reagent for detecting a component of zygomycota.

[33]

The reagent kit according to [31] or [32] above, wherein the reagent containing an acid component is the agent as recited in [23] or [24] above.

[34]

The reagent kit according to any one of [31] to [33] above, wherein the reagent for detecting a component of zygomycota is an anti-chitosan antibody.

[35]

The reagent kit according to any one of [31] to [34] above, the kit being a diagnosis kit for zygomycosis.

[36]

The reagent kit according to any one of [31] to [34] above, the kit being a diagnosis kit for mucormycosis or entomophthoramycosis.

<1> Measuring Method of the Present Invention

The present invention provides a method for measuring zygomycota, characterized in that the method comprises measuring zygomycota in a specimen that was subjected to an acid treatment (hereinafter referred to as the "measuring method of the present invention"). The measuring method of the present invention may be employed as, for example, a detection method of zygomycota, a sensing method of zygomycota, a quantification method of zygomycota, a detection method of zygomycosis, a sensing method of zygomycosis, or a quantification method of zygomycosis. Alternatively, the measuring method of the present invention may be employed as, for example, a method for collecting data for the diagnosis of zygomycosis, characterized in that the method comprises performing measurement of zygomycota (inspection of specimen) in a sample (specimen) that was subjected to an acid treatment; and collecting data for diagnosing whether an animal is infected with zygomycosis or not.

<2> Specimen Preparation Agent of the Present Invention

As described above, in the present invention, a specimen for measurement of zygomycota is prepared through an acid treatment. In view of simplicity of practice, the acid treatment may be performed by coexisting an untreated specimen with an acid component. Accordingly, the present invention provides an agent for preparing a specimen for measurement of zygomycota, characterized in that the agent contains an acid component (hereinafter referred to as the "specimen preparation agent of the present invention"). The agent characterized by containing an acid component may serve as an acid treatment agent for a specimen to be subjected to measurement of zygomycota. The specimen preparation agent of the present invention and the acid treatment agent may be produced through any method including a step of incorporating an acid component into the agent. Also, the specimen preparation agent of the present invention and the acid component are preferably used for the acid treatment of a specimen to be subjected to the measuring method of the present invention.

<3> Specimen Preparation Method of the Present Invention

As described above, a specimen for measurement of zygomycota can be prepared through subjecting an untreated specimen to an acid treatment. Accordingly, the present invention provides a method for preparing a specimen for measurement of zygomycota, characterized in that the method comprises subjecting an untreated specimen to an acid treatment, thereby converting the specimen to a specimen for measurement of zygomycota (hereinafter, the method referred to as the "specimen preparation method of the present invention"). The specimen preparation method of the present invention can be preferably employed as a method of the acid treatment carried out for preparing a specimen to be subjected to the measuring method of the present invention. In the specimen preparation method of the present invention, the acid treatment is preferably a treatment of coexisting an untreated specimen with an acid component. The treatment of coexisting an untreated specimen with an acid component is preferably a treatment of coexisting an untreated specimen with the specimen preparation agent of the present invention.

<4> Reagent Kit of the Present Invention

In the present invention, a practically advantageous embodiment of measurement of zygomycota employs a reagent kit, characterized in that the kit comprises at least one of a reagent containing an acid component and a reagent for detecting a component of zygomycota (hereinafter referred to as the "reagent kit of the present invention"). The reagent kit of the present invention can be preferably used for the measuring method of the present invention. The reagent containing an acid component is preferably the specimen preparation agent of the present invention. The reagent for detecting a component of zygomycota is preferably an anti-chitosan antibody. The reagent kit of the present invention may further contain, in addition to the aforementioned components, any additional component. The additional component may be appropriately selected in accordance with the mode of measurement of zygomycota. The reagent kit of the present invention may be employed as a diagnosis kit for zygomycosis, such as a diagnosis kit for mucormycosis or entomophthoramycosis.

<5> Acid Treatment

In the present invention, the acid treatment is performed as a pretreatment of a specimen to be subjected to measurement of zygomycota. In the acid treatment, an untreated specimen is acidified by causing the specimen to be placed under acidic conditions. In a practically advantageous embodiment of the acid treatment, the specimen is caused to be co-present with an acid component. The thus-acid-treated specimen may be a specimen that was subjected to a treatment of coexisting the specimen with an acid component.

<6> Acid Component

In the present invention, the acid component may be an organic acid or an inorganic acid. The organic acid is preferably a carboxylic acid. The carboxylic acid is preferably acetic acid, formic acid, or citric acid. The inorganic acid is preferably a hydrogen halide, sulfuric acid, or phosphoric acid. The hydrogen halide is preferably hydrogen chloride (hydrochloric acid). These acid components may be used singly or in combination of two or more species.

<7> Measurement of Zygomycota

In the present invention, measurement of zygomycota may be carried out by use of, for example, a reagent for detecting a component of zygomycota. The reagent for detecting a component of zygomycota is preferably an anti-chitosan antibody. In the present invention, measurement of zygomycota may be carried out through, for example, immunoassay. The immunoassay preferably employs an anti-chitosan antibody. Examples of the immunoassay include enzyme immunoassay (EIA), immunochromatography, immunoblotting, a flocculation method, turbidimetry, and nephelometry. An example of the flocculation method is latex flocculation. The enzyme immunoassay may be enzyme-linked immunosorbent assay (ELISA).

<8> Specimen

In the present invention, no particular limitation is imposed on the specimen to be subjected to measurement of zygomycota, so long as the specimen is a material which can contain zygomycota. The specimen is preferably a specimen derived from an animal such as human, and the present invention is preferably applied to inspection of specimen. Examples of the specimen derived from an animal include a specimen recovered from an animal body and a specimen obtained by bringing a liquid into contact with an animal body and recovering the liquid. No particular limitation is imposed on the liquid to be brought into contact with an animal body, so long as the liquid is compatible with a biological body. An example of the liquid is physiological saline. The liquid brought into contact with an animal body and then recovered can be subjected to an acid treatment as is, as a specimen to be subjected to measurement of zygomycota. The specimen recovered from an animal body is preferably a blood-derived sample. The blood-derived sample is particularly preferably a serum or plasma. The liquid brought into contact with an animal body and then recovered is preferably a bronchoalveolar lavage fluid (BALF) sample. Also, the animal is preferably an animal suffering from zygomycosis or possibly suffering from zygomycosis. Examples of the zygomycosis include mucormycosis and entomophthoramycosis.

In the present invention, the specimen for measurement of zygomycota is prepared through an acid treatment. In the present invention, the specimen for measurement of zygomycota may be a specimen that was subjected to an acid treatment followed by neutralization.

In the description hereinbelow, the following abbreviation may be used.

GlcN: glucosamine
GlcNAc: N-acetyl-D-glucosamine
CTS: chitosan
CTS6: chitosan hexamer
GCTS: glycol chitosan
CTN: chitin
EGCTN: ethylene glycol chitin
CTSpAb: anti-chitosan polyclonal antibody
CTSmAb: anti-chitosan monoclonal antibody
PBS: phosphate-buffered saline Effects of the Invention According to the present invention, zygomycota contained in a specimen can be measured at high sensitivity. The present invention may serve as means for realizing a serological diagnosis for zygomycosis such as mucormycosis or entomophthoramycosis, the means being effective for an early diagnosis thereof.

MODES FOR CARRYING OUT THE INVENTION

1. Preparation of Acid-Treated Specimen

Figure 1:
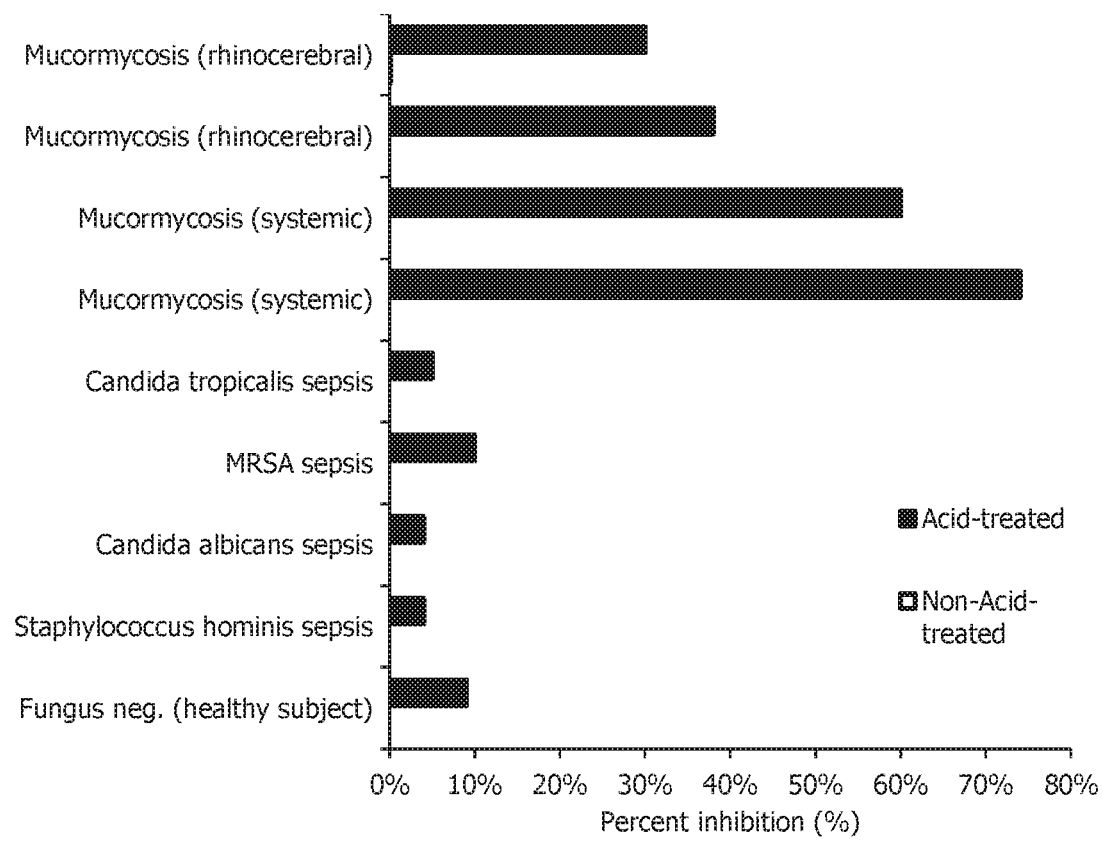
FIG. 1 A graph showing percent decrease in absorbance (i.e., percent inhibition) obtained as the result of measurement of zygomycota for human sera of subjects suffering from infections such as mycosis in competitive ELISA employing an anti-chitosan antibody (comparison between cases with an acid treatment and cases without an acid treatment).

In the present invention, the specimen for measurement of zygomycota is prepared through the aforementioned acid treatment. In the present invention, no particular limitation is imposed on the means for acid treatment, so long as the means causes an untreated specimen to be under acidic conditions (i.e., acid treatment). An example of the means is coexisting the untreated specimen with a cation exchanger, activated carbon (acidic carbon), or an acid component. The acid treatment is preferably a treatment of causing an untreated specimen to be co-present with an acid component, from the viewpoint of simplicity of practice and cost of the treatment. The concept "co-present" refers to realizing a state in which one object can be into contact with another object. Specifically, co-presence of a specimen with an acid component can be realized by adding an acid component to a specimen, or adding a specimen to an acid component. Preferably, the acid treatment is carried out in liquid. The liquid in which the acid treatment is carried out is preferably water or an aqueous solution.

1-1: Acid Component

No particular limitation is imposed on the acid component, so long as the component exhibits acidity when it is co-present with water. The acid component may be a compound which releases hydrogen ions when it is co-present with water, or a compound which releases hydrogen ions when it is ionized. In other words, the acid component may be an Arrhenius acid. Examples of the acid component include an oxoacid, an organic acid, and an inorganic acid. Examples of the oxoacid include a carboxylic acid, a sulfonic acid, sulfuric acid, phosphoric acid, nitric acid, and a halogen oxoacid. Examples of the organic acid include a carboxylic acid and sulfonic acid. Examples of the carboxylic acid include acetic acid, formic acid, citric acid, and oxalic acid. Examples of the inorganic acid include a hydrogen halide, sulfuric acid, phosphoric acid, nitric acid, and a halogen oxoacid. Examples of the hydrogen halide include hydrogen chloride (hydrochloric acid). Examples of the halogen oxoacid include a hypohalous acid and a perhalogenic acid. Examples of the hypohalous acid include hypochlorous acid, hypobromous acid, and hypoiodous acid. Examples of the perhalogenic acid include perchloric acid, perbromic acid, and periodic acid. When the acid component is an organic acid, the acid component is preferably a carboxylic acid, and particularly preferably acetic acid, formic acid, or citric acid. When the acid component is an inorganic acid, the acid component is preferably a hydrogen halide, sulfuric acid, or phosphoric acid, and more preferably a hydrogen halide. The hydrogen halide is particularly preferably hydrogen chloride (hydrochloric acid).

Alternatively, the acid component may be, for example, an acid anhydride or a polyoxoacid. Examples of the acid anhydride include a carboxylic anhydride and phosphoric anhydride acid, and specific examples include acetic anhydride and pyrophosphoric acid. Examples of the polyoxoacid include polyphosphoric acid.

Still alternatively, the acid component may be a salt, so long as the component exhibits acidity when it is co-present with water. Examples of the salt include an ammonium salt and a sodium salt, and specific examples include dihydrogen ammonium phosphate, dihydrogen ammonium citrate, dihydrogen sodium phosphate, and dihydrogen sodium citrate.

No particular limitation is imposed on the form of the acid component, and it may be a solid, a liquid, or a gas. The liquid-form acid component may be prepared by dissolving a solid-form or gas-form acid component in a solvent such as water.

In the acid treatment, these acid components may be used singly or in combination of two or more species.

1-2: Specimen

No particular limitation is imposed on the specimen, so long as it can contain zygomycota. An example of the specimen is a specimen derived from an animal. Examples of the animal include, in addition to a human, animals which can suffer from zygomycosis such as mucormycosis or entomophthoramycosis. Examples of such animals include mammals such as monkey, dog, cat, rabbit, horse, and bovine; and bird (Aves). Recently, since zygomycosis infection caused from pet animals and zygomycosis infection of pet animals have become serious problems, specimens derived from non-human animals are also important as an origin of a specimen. The specimen derived from an animal may be a specimen recovered from an animal body or a specimen obtained by bringing a liquid into contact with an animal body and recovering the liquid.

Examples of the specimen derived from an animal include sputum, cerebrospinal fluid, nasal swab, pharyngeal swab, nasal aspirate, ascites, bronchoalveolar lavage fluid (BALF), a biopsy specimen, and a blood-derived sample. Examples of the specimen recovered from an animal body include sputum, cerebrospinal fluid, nasal swab, pharyngeal swab, nasal aspirate, ascites, a biopsy specimen, and a blood-derived sample. An example of the specimen obtained by bringing a liquid into contact with an animal body and recovering the liquid is bronchoalveolar lavage fluid (BALF). Bronchoalveolar lavage fluid (BALF) is typically known as a liquid obtained by injecting physiological saline or the like into the bronchi so as to wash alveoli, and recovering the wash liquid.

The blood-derived sample may be blood as is or a blood sample containing an additional component such as an anti-coagulant. Alternatively, the blood-derived sample may be a blood fraction (e.g., a serum or plasma) obtained through fractionation or purification of a blood sample. Among these blood-derived samples, a serum and plasma are particularly preferred. In one general procedure, a serum may be obtained by allowing a blood sample collected from an animal to stand or subjecting a blood sample to centrifugation, and recovering the supernatant. In one general procedure, plasma may be obtained by adding an anti-coagulant to a blood sample collected from an animal, allowing the sample to stand or subjecting the sample to centrifugation, and recovering the supernatant.

No particular limitation is imposed on the form of the specimen, and the specimen may be liquid or solid. Examples of the liquid specimen include the aforementioned liquid components such as sputum, cerebrospinal fluid, nasal swab, pharyngeal swab, nasal aspirate, ascites, bronchoalveolar lavage fluid (BALF), and a blood-derived sample, and a suspension of a biopsy specimen. Examples of the solid specimen include the aforementioned biopsy specimen, and dried (e.g., lyophilized) powder of the liquid components (e.g., sputum, cerebrospinal fluid, nasal swab, pharyngeal swab, nasal aspirate, ascites, bronchoalveolar lavage fluid (BALF), and a blood-derived sample). The specimen may be a liquid specimen as is, or a liquid specimen which has been appropriately concentrated or diluted. Alternatively, a liquid specimen may be prepared by appropriately dissolving a solid specimen.

1-3: Acid Treatment

In the present invention, the acid treatment is a treatment of acidifying a specimen and may be carried out by causing an untreated specimen to be placed under acidic conditions. No particular limitation is imposed on the pH at the time when the acid treatment of the specimen is performed (hereinafter the period of time referred to as "during acid treatment"), so long as the pH is 6 or lower, and the pH may be adjusted to any value which is 6 or lower. The pH during acid treatment may be appropriately adjusted in accordance with the type of the specimen and the mode of measurement of zygomycota. The pH (including the lower limit) may be, for example, 0 or higher, 0.5 or higher, 1 or higher, 2 or higher, 3 or higher, or 3.5 or higher. The pH (including the upper limit) may be, for example, 6 or lower, 5.5 or lower, 5 or lower, or 4.5 or lower. More specifically, the pH may be, for example, 0 to 6, 0.5 to 5.5, 0 to 5, 0.5 to 5, 1 to 5, 2 to 5, 3 to 5, or 3.5 to 4.5.

No particular limitation is imposed on the concentration of acid component during acid treatment, in the case where the specimen is co-present with the acid component, and the pH may be appropriately adjusted in accordance with factors such as the type of the acid component and the target pH. The concentration (including the lower limit) may be, for example, 0.001 mM or higher, 0.01 mM or higher, 0.1 mM or higher, 1 mM or higher, 10 mM or higher, 50 mM or higher, or 100 mM or higher. The concentration (including the upper limit) may be, for example, 1 M or lower, 500 mM or lower, or 250 mM or lower. More specifically, the concentration may be 0.001 mM to 1 M, 0.01 mM to 1 M, 0.1 mM to 1 M, 1 mM to 1 M, 10 mM to 1 M, 50 mM to 500 mM, 100 mM to 500 mM, or 100 mM to 250 mM. Notably, when two or more kinds of acid components are used, the concentration of acid component is the sum of the concentration of each acid component. The concentration may be the final concentration of acid component after addition of the acid component to the specimen of interest.

No particular limitation is imposed on the temperature during acid treatment, and the temperature may be adjusted to any level. The acid treatment may be carried out, for example, at ambient temperature (15 to 25° C.), or a temperature lower or higher than ambient temperature. The temperature (including the lower limit) may be, for example, 0° C. or higher, 4° C. or higher, 10° C. or higher, or 20° C. or higher. The temperature (including the upper limit) may be, for example, 125° C. or lower, 100° C. or lower, 75° C. or lower, 50° C. or lower, or 37° C. or lower. More specifically, the temperature may be the aforementioned ambient temperature, 0° C. to 125° C., 4° C. to 100° C., 10° C. to 75° C., or 20° C. to 75° C.

The acid treatment may be carried out at room temperature (24 to 26° C.) or in a state where the specimen is placed under cooling or heating. Cooling or heating of the specimen may be performed by means of an apparatus such as a heat block, a water bath, an oil bath, or an air bath.

No particular limitation is imposed on the time of carrying out the acid treatment; i.e., the period of time from the start to the termination of the acid treatment (hereinafter the time referred to as a "treatment time"). The treatment time (including the shorter limit) may be, for example, 5 seconds or longer, 30 seconds or longer, 1 minute or longer, or 5 minutes or longer. The treatment time (including the longer limit) may be, for example, 24 hours or shorter, 2 hours or shorter, 1 hour or shorter, or 30 minutes or shorter. More specifically, the treatment time may be 5 seconds to 24 hours, 30 seconds to 2 hours, 1 minute to 1 hour, or 5 minutes to 30 minutes.

The specimen subjected to the acid treatment may be used as a specimen for measurement of zygomycota, without performing any further treatment. However, when the measurement is carried out with a component unsuited for the measurement under acidic conditions (e.g., a protein such as an antibody), a specimen after termination of the acid treatment is preferably used for the measurement of zygomycota.

The acid treatment can be terminated by, for example, adjusting the pH of the specimen to a level higher than the pH suitable for the acid treatment, preferably to a neutral or basic pH level. The acid treatment can be terminated by adding a neutral component or a basic component to the specimen or removing an added component for acidifying the specimen (e.g., the acid component) from the specimen. In one specific mode of terminating the acid treatment, the pH of the specimen is adjusted to 6.5 or higher, preferably 7 or higher.

Note that, in the termination of the acid treatment, degradation of a certain component through hydrolysis under alkaline conditions may impede the measurement of zygomycota. Thus, preferably, the specimen has not been placed under strongly basic conditions. The pH of the strongly basic conditions may be, for example, 12 or higher, 12.5 or higher, 13 or higher, 13.5 or higher, or 14 or higher.

The termination of the acid treatment may be carried out by adjusting the pH of the specimen. The target pH is preferably 6.5 to 12, more preferably 7 to 12, still more preferably 7 to 10, yet more preferably 7 to 8. The specimen that was subjected to the acid treatment and neutralization may be used as a specimen for measurement of zygomycota without performing any further treatment. In the present invention, the pH of the specimen for measurement of zygomycota is preferably adjusted, after the acid treatment, to a level satisfying the aforementioned conditions.

In the acid treatment, the specimen may be subjected to dilution or dissolution. No particular limitation is imposed on the dilution factor of the specimen. The dilution factor (including the lower limit) may be, for example, more than 1, 1.1 or more, 2 or more, 5 or more, or 10 or more. The dilution factor (including the upper limit) may be, for example, 500 or less, 200 or less, or 100 or less. More specifically, the dilution factor may be, for example, more than 1 to 500, 1.1 to 500, 2 to 200, 5 to 200, or 10 to 100.

The acid treatment may be performed once or 2 or more times. In one possible mode of the acid treatment, a specimen is allowed to be placed under acidic conditions, the product is further neutralized, and the product may be further acidified. In the case where the acid treatment is performed a plurality of times, the same or different conditions as or from those of the acid treatment (pH, the type of acid component, the concentration of acid component, temperature, and time, etc.) may be employed.

1-4: Specimen Preparation Agent of the Present Invention

The specimen preparation agent of the present invention contains any of the above-exemplified acid components and is employed for acidifying the specimen. The specimen preparation agent of the present invention may be a liquid agent or a solid agent that is dissolved upon use (e.g., powder, granule, or tablet). The specimen preparation agent of the present invention may be an acid component as is or an agent prepared by dissolving or diluting an acid component in or with a solvent such as water. Also, in addition to the acid component and solvent, the specimen preparation agent of the present invention may further contain other components for the purposes of formulation and the like. No particular limitation is imposed on the type of additional components, so long as the components are pharmacologically acceptable for preparing reagents or diagnostic agents. Examples of such components include an alkali metal salt, an alkaline earth metal salt, and other additives. Examples of the additives include a stabilizer, a preservative, an antiseptic, an emulsifier, a surfactant, a moisturizer, a suspending agent, a dispersant, an osmotic agent, a tonicity agent, a buffer, a pH-adjuster, an antioxidant, an excipient, a binder, a disintegrant, a lubricant, and a colorant.

In the specimen preparation agent of the present invention, the acid component may be present in a non-ionized form, an ionized form, or a mixture of non-ionized and ionized form.

In the specimen preparation agent of the present invention, no particular limitation is imposed on the content of acid component (weight percent concentration (w/w)), and any concentration may be employed. The concentration (w/w) (including the lower limit) may be, for example, 0.001% or higher, 0.01% or higher, 0.1% or higher, 1% or higher, 5% or higher, 10% or higher, 25% or higher, or 50% or higher. The concentration (w/w) (including the upper limit) may be, for example, 100% or lower, 75% or lower, 50% or lower, 25% or lower, 10% or lower, 5% or lower, or 1% or lower.

No particular limitation is imposed on the usage of the specimen preparation agent of the present invention, and the usage may be appropriately predetermined in accordance with the type, concentration, etc. of the acid component contained in the specimen preparation agent of the present invention. The specimen preparation agent of the present invention may be used in such an amount that the amount of acid component is suitable for the acid treatment of the specimen, as mentioned above.

The specimen preparation agent of the present invention may be produced through a technique generally employed in preparation of reagents or diagnostic agents.

Through subjecting a specimen to be subjected to measurement of zygomycota to the acid treatment by use of the specimen preparation agent of the present invention, the specimen becomes suitable for the measurement of zygomycota, whereby measurement of zygomycota of interest can be performed at high sensitivity.

1-5: Specimen Preparation Method of the Present Invention

The specimen preparation method of the present invention is a method of transforming, through the acid treatment, an untreated specimen (i.e., a specimen to be subjected to measurement of zygomycota) into a specimen for measurement of zygomycota (a specimen suited for measurement of zygomycota). The specimen preparation method of the present invention may include an additional step performed before or after the acid treatment step. The additional step may be carried out in parallel with the acid treatment step. The specimen preparation method of the present invention may further include, for example, a step of terminating the acid treatment, a step of dissolving a solid specimen, or a step of diluting or concentrating a liquid specimen. Also, the specimen preparation method of the present invention may further include, for example, a step of heating or cooling a prepared specimen so that the temperature of the specimen becomes suitable for measurement of zygomycota. Further, the specimen preparation method of the present invention may include, for example, a step of modulating the pH of the prepared specimen so that the pH of the specimen becomes suitable for measurement of zygomycota.

According to the specimen preparation method of the present invention, a specimen can be converted to a specimen suitable for measurement of zygomycota, whereby measurement of zygomycota of interest can be performed at high sensitivity.

2. Zygomycota Measurement 2-1: Measurement Technique

As described above, the measuring method of the present invention is directed to a method for measuring zygomycota. Specifically, zygomycota serving as a measuring target in the present invention is zygomycota that was subjected to an acid treatment. Thus, in one embodiment, the measuring target is a component derived from the corresponding zygomycota. The zygomycota serving as a measuring target in the present invention may be cell bodies thereof, cell bodies of a fragmentated zygomycota, or a part or a component of the cell bodies. Also, the zygomycota serving as a measuring target in the present invention may be a live bacterium or a dead cell thereof such as an inactivated cell. The measurement of zygomycota may be carried out, for example, by use of a reagent for detecting a component of zygomycota (i.e., a regent for detecting a component derived from the target zygomycota).

No particular limitation is imposed on the component of zygomycota serving as the measuring target. Examples of the component include nucleic acid, protein, lipid, and carbohydrate. The component is preferably a component consisting of the same common structure among various species of zygomycota, from the viewpoint of comprehensive determination of the presence or absence of zygomycota in a specimen. More preferably, the component of zygomycota serving as the measuring target is a lipid or a carbohydrate, with a carbohydrate being more preferred. The carbohydrate is preferably a saccharide, with chitosan being more preferred. Particularly preferably, the measurement of zygomycota is performed against chitosan as a measuring target. In the present invention, the term "measurement" is defined as a comprehensive concept including detection, sensing, and quantification. That is, the measurement of zygomycota in the present invention encompasses detection of zygomycota, sensing of zygomycota, and quantification of zygomycota.

The aforementioned detection reagent is a reagent which causes a physical or chemical change in a component of zygomycota or the reagent as is, upon coming into contact with the component of zygomycota. The change includes binding, transfer, dislocation, addition, elimination, decomposition, oxidation, reduction, labeling, coloring, and light emission. Such a change can be measured, for example, as a change in a chromatographic peak profile, a contrast, or a value measured by means of an analytical apparatus, or as a signal detected in accompany with the change. Alternatively, the change may be detected by use of a reagent for labeling or detecting the aforementioned detection reagent or a reaction product formed through contact with the aforementioned detection reagent. The reagent may be a reagent which causes a physical or chemical change in the aforementioned detection reagent, a reaction product formed through contact with the aforementioned detection reagent, or the reagent as is. Examples of the aforementioned detection reagent and the reagent for labeling or detecting the aforementioned detection reagent or a reaction product formed through contact with the aforementioned detection reagent include an antibody which can bind thereto.

The aforementioned detection reagent is preferably a reagent which realizes specific detection of a measuring target. Examples of the reagent include an antibody. The measurement of zygomycota is preferably performed through immunoassay. As described above, the measurement of zygomycota is particularly preferably performed against chitosan as a measuring target. Thus, the detection reagent is particularly preferably an antibody which can bind to chitosan (i.e., an anti-chitosan antibody).

The antibody employed in immunoassay may be a polyclonal antibody, a monoclonal antibody, or a mixture thereof.

The aforementioned antibody may be an antibody as is or an antibody labeled with another substance (i.e., a labeled antibody). Examples of the labeled antibody include an enzyme-labeled antibody, a fluorescent-labeled antibody, and a biotin-labeled antibody.

No particular limitation is imposed on the type of immunoglobulin of the aforementioned antibody. When the antibody is an anti-chitosan antibody, the antibody is preferably produced by immunizing a bird (Aves), for the reason mentioned below, with an IgY antibody being more preferred. Since IgY is an immunoglobulin absent in a mammal, the IgY antibody can be particularly preferably used, in the case where a specimen of measuring target is derived from a mammal.

The aforementioned antibody may be a mixture of two or more kinds of antibodies having the same epitope on the component of measuring target, or a mixture of two or more kinds of antibodies having different epitopes on the component of measuring target.

In the present invention, the antibody may be used as a sole component or as an antibody formulation containing other components in addition to the antibody. Examples of the other component include an alkali metal salt, an alkaline earth metal salt, a surfactant, a buffer, and components, with the exception of the antibody, derived from an animal immunized with the antigen.

No particular limitation is imposed on the content of antibody in the aforementioned antibody formulation (weight volume percent concentration (w/v)), and the content can be tuned to any value. The concentration (w/v) (including the lower limit) may be, for example, 0.001% or higher, 0.01% or higher, 0.1% or higher, 1% or higher, 5% or higher, 10% or higher, 25% or higher, or 50% or higher. The concentration (w/v) (including the upper limit) may be, for example, 100% or lower, 75% or lower, 50% or lower, 25% or lower, 10% or lower, 5% or lower, or 1% or lower.

No particular limitation is imposed on the mode of immunoassay, and it can be carried out through a known method employed in an antigen assay with antigen-antibody reaction. Examples of preferred immunoassay techniques include enzyme immunoassay (EIA or ELISA), immunochromatography, immunoblotting (e.g., dot blotting, slot blotting, or spot blotting), a flocculation method, turbidimetry, and nephelometry. The flocculation method is preferably latex flocculation.

Examples of the ELISA technique include (a) adding an antibody (a detection antibody) to a specimen immobilized on a plate, and assaying the antigen contained in the specimen (binding method); (b) adding a specimen and an antibody (a detection antibody) to an antibody immobilized on a plate (an immobilized antibody), and assaying the antigen contained in the specimen (sandwich method); and (c) adding a specimen (a competitive substance) and an antibody (a detection antibody) to an antigen immobilized on a plate, and assaying the antigen contained in the specimen (competitive method, inhibition method). Among these ELISA techniques, competitive method (hereinafter referred to as "competitive ELISA") and sandwich method (hereinafter referred to as "sandwich ELISA") is preferred, since a large amount of plates for the assay can be prepared and stored before the assay. Of these, sandwich ELISA is more preferred.

In competitive ELISA or sandwich ELISA, a specimen subjected to the acid treatment and the detection antibody may be added separately to a plate in any order, or may be mixed preliminarily and added to a plate. In these ELISA techniques, the period of time when the two components (a specimen and the detection antibody) are co-present before being added to a plate is preferably several hours to one day or thereabout. Specifically, the time may be, for example, 1 to 24 hours, 12 to 24 hours, or 18 to 24 hours.

No particular limitation is imposed on the two kinds of antibodies (the immobilized antibody and the detection antibody) employed in the sandwich ELISA, so long as they can bind to a component of zygomycota. The two antibodies may recognize an identical epitope or different epitopes. The two kinds of antibodies may be identical to or different from one another.

2-2: Antibody

The antibodies employed in the present invention may be produced through a known method employed for production of an antibody, and no particular limitation is imposed on the method. In a typical mode of antibody production, an animal is immunized with a corresponding antigen. In the present invention, the antigen may be zygomycota as is, a fragment thereof, or a component thereof. Alternatively, a complex of the antigen fused with another substance may also be used for enhancing immunogenicity. The complex may be formed with a protein, and specific examples of the protein include bovine serum albumin (BSA). A mixture of the antigen with an antigenic adjuvant may also be used for immunization of an animal.

As described above, the component of zygomycota serving as the antigen is preferably chitosan. No particular limitation is imposed on the origin of chitosan serving as the antigen, and chitosan other than chitosan extracted from zygomycota (e.g., commercial chitosan) may also be used. An example of the chitosan serving as the antigen is chitosan obtained through N-deacetylation of chitin. Chitin provided in the present invention may be derived from a crustacean such as crab or shrimp. No particular limitation is imposed on the polymerization degree of chitosan (i.e., the molecular weight of chitosan), and the chitosan may be a polymer or an oligomer (i.e., oligosaccharide). Among these, an oligomer is preferred, since a high reaction yield can be attained when a complex thereof is formed through fusion with another substance. An example of such an oligomer is a hexamer thereof. The chitosan must have an epitope sequence (i.e., repeatedly polymerized GlcN residues) to which an anti-chitosan antibody can bind. The chitosan may comprise only GlcN residues as saccharide residues. Alternatively, the chitosan may comprise GlcN residues and GlcNAc residues as saccharide residues. No particular limitation is imposed on the number of the GlcN residues polymerized in the epitope sequence, and it is preferably 3 or higher. No particular limitation is imposed on the deacetylation degree of the chitosan (hereinafter referred to as a "deacetylation degree"). Specifically, the deacetylation degree may be, for example, 60% or higher, 70% or higher, 80% or higher, 90% or higher, 95% or higher, 98% or higher, 99% or higher, or 100%. The deacetylation degree is preferably as higher as possible.

The deacetylation degree of chitosan is defined as the ratio of the total number of the GlcN residues to the sum of the GlcN residues and the GlcNAc residues forming the backbone of chitosan. That is, the deacetylation degree of chitosan is defined as the percentage obtained by dividing the total number of the GlcN residues by the sum of the GlcN residues and the GlcNAc residues. The deacetylation degree may be determined through, for example, a known method such as nuclear magnetic resonance (NMR), infrared absorption spectrometry (IR), or colloidal titration.

An animal which is immunized to produce an anti-chitosan antibody is immunized by the aforementioned chitosan. No particular limitation is imposed on the animal, so long as it can produce an anti-chitosan antibody. Preferably, the animal inherently does not have an anti-chitosan antibody. Examples of the animal include mammals and birds (Aveses), with birds (Aveses) being preferred. Among these, *Gallus gallus domesticus* is particularly preferred.

The antibody may be a polyclonal antibody, a monoclonal antibody, or a mixture thereof. The anti-chitosan polyclonal antibody may be obtained from, for example, components or cells derived from chitosan-immunized animals. More specifically, the anti-chitosan antibody may be obtained from a body fluid, ovum cells, etc. of chitosan-immunized animals. Examples of the animal body fluid include blood, a serum, plasma, and ascites. The anti-chitosan monoclonal antibody may be obtained from, for example, a hydridoma of an antibody-producing cell of chitosan-immunized animals with a myeloma cell, or a culture liquid of the hybridoma.

Alternatively, the anti-chitosan monoclonal antibody may also be obtained from cells transfected with an expression vector for the anti-chitosan antibody or a culture liquid of the transfected cells. The transfected cells may be produced through, for example, a method disclosed in a document (WO 2011/049082) or a method using a commercial kit such as Mammalian Power Express System (product of Toyobo). The transfected cells may be cells for transient expression or cells for stable expression.

In the present invention, an animal-derived component, animal cells, hybridoma cells, or a culture liquid of hydridoma cells may be used as the antibody, without performing any further treatment. Alternatively, a suspension extract from animal cells or hybridoma cells, or a cell residue thereof may also be used as the antibody. Still alternatively, a fraction obtained by purifying any of these may also be used as the antibody. The technique for suspending cells may be appropriately chosen in accordance with the cell species. Examples of the suspension technique include homogenization, ultrasonication, freezing and thawing, and addition of a surfactant.

The antibody may be purified through any known technique employable for isolation or purification of a protein. Examples of the purification technique of the antibody include ammonium sulfate precipitation and various chromatographic techniques. Alternatively, the antibody may be purified by use of a component which can bind to an antibody such as protein A, protein G, or protein L. The purification degree of antibody may be any level.

2-3: Type of Zygomycota

In the present invention, no particular limitation is imposed on the type of zygomycota subjected to measurement as a measuring target. Zygomycota is defined as a fungus belonging to Zygomycota. Examples of the fungus include those belonging to Zygomycetes and Trichomycetes. Examples of the fungus belonging to Zygomycetes include those belonging to Dimargaritales, Endogonales, Entomophthorales, Glomales, Kickxellales, Mucorales, or Zoopagales. Examples of the fungus belonging to Trichomycetes include those belonging to Amoebidiales, Asellariales, Eccrinales, or Harpellales.

Zygomycota is also defined as a fungus belonging to Glomeromycota, Entomophthoromycotina, Kickxellomycotina, Mucoromycotina, or Zoopagomycotina. Examples of the fungus belonging to Glomeromycota include those belonging to Glomeromycetes. Examples of the fungus belonging to Glomeromycetes include those belonging to Archaeosporales, Diversisporales, Glomerales, or Paraglomerales. Examples of the fungus belonging to Entomophthoromycotina include those belonging to Entomophthorales. Examples of the fungus belonging to Kickxellomycotina include those belonging to Asellariales, Dimargaritales, Harpellales, or Kickxellales. Examples of the fungus belonging to Mucoromycotina include those belonging to Endogonales, Mortierellales, or Mucorales. Examples of the fungus belonging to Zoopagomycotina include those belonging to Zoopagales.

Examples of the fungus belonging to Mucorales include those belonging to Mucoraceae, Cunninghamellaceae, Saksenaeaceae, or Thamnidiaceae. Examples of the fungus belonging to Mucoraceae include *Absidia, Apophysomyces, Lichtheimia, Mucor, Rhizomucor*, or *Rhizopus*. Examples of the fungus belonging to Cunninghamellaceae include those belonging to *Cunninghamella*. Examples of the fungus belonging to Saksenaeaceae include those belonging to *Saksenaea*. Examples of the fungus belonging to Thamnidiaceae include those belonging to *Cokeromyces*.

Specific examples of the fungus belonging to Mucorales include those belonging to *Absidia butleri, Absidia corymbifera, Apophysomyces elegans, Apophysomyces trapeziformis, Lichtheimia corymbifera, Mucor circinelloides, Mucor plumbeus, Mucor racemosus, Mucor ramosissimus, Mucor rouxii, Rhizomucor pusillus, Rhizopus arrhizus, Rhizopus microspores, Rhizopus oryzae, Rhizopus stolonifer, Cunninghamella bertholletiae, Cunninghamella* echinulata, *Saksenaea vasiformis*, or *Cokeromyces* recurvatus.

Examples of the fungus belonging to Entomophthorales include those belonging to Entomophthoraceae or Basidiobolaceae. Examples of the fungus belonging to Entomophthoraceae include those belonging to *Conidiobolus*. Examples of the fungus belonging to Basidiobolaceae include those belonging to *Basidiobolus*.

Specific examples of the fungus belonging to Entomophthorales include *Conidiobolus brefeldianus, Conidiobolus coronatus, Conidiobolus incongruus, Conidiobolus lamprauges, Basidiobolus meristosporus*, or *Basidiobolus ranarum*.

2-4: Other Steps and Derivation of Measurement Results

The measuring method of the present invention may further include any additional step, in addition to the aforementioned step of subjecting a specimen to an acid treatment and the step of bringing a reagent for detecting a component of zygomycota into contact with zygomycota, to thereby detect the zygomycota (hereinafter referred to as "zygomycota detecting step"). Examples of the additional step include a step of converting the pH of the acid-treated specimen to a neutral or basic level, so as to terminate the acid treatment (neutralization step). The step of terminating the acid treatment is preferably carried out, for example, when the reagent for detecting a component of zygomycota does not suitably work under acidic conditions. For example, when the reagent for detecting a component of zygomycota is a protein such as an antibody, the protein might be denatured under acidic condition or inhibited from binding to a component of zygomycota. In such a case, the neutralization step may be preferably carried out before the zygomycota detecting step.

Examples of the additional step also include a step of transforming a measurement value obtained in the zygomycota detecting step into another value. The additional step is, for example, a step of transforming a measurement value obtained in the zygomycota detecting step into a content (amount or number) of zygomycota in a specimen, with reference to the relationship between a measurement value obtained through contact of a concentration-known standard substance with the reagent for detecting a component of zygomycota and the concentration of the standard substance (i.e., a calibration curve). This step may be a step of transforming a measurement value obtained in the zygomycota detecting step into a value indicating the development of zygomycosis, particularly when the specimen is derived from an animal. The "calibration curve" may be obtained by carrying out the zygomycota detecting step by use of a standard substance instead of a specimen to be subjected to measurement of zygomycota. The standard substance may be zygomycota as is. However, a component of zygomycota is preferably used in practice as the standard substance. As described above, an example of the component of zygomycota is chitosan. When zygomycota is used as a standard substance, zygomycota inactivated by means of a high-pressure steam sterilizer (an autoclave) or the like is preferably employed from the viewpoint of safety. Examples of the measurement value obtained in the zygomycota detecting step include a value obtained by use of a fluorescence spectrometer (fluorescent intensity) and a value obtained by use of a spectrophotometer (absorbance).

According to the measuring method of the present invention, zygomycota contained in a specimen can be measured at high sensitivity.

The measuring method of the present invention enables, for example, to determine whether or not a specimen contains zygomycota; to identify a fungus contained in a specimen to be or not to be zygomycota; and to quantitatively determine the number of zygomycota cells or the degree of development of zygomycosis. Thus, one embodiment of the measuring method of the present invention is a method for determining whether or not a specimen contains zygomycota; a method for identifying a fungus contained in a specimen to be or not to be zygomycota; a method for determining whether or not the mycosis is caused by zygomycota; a method for determining whether or not the mycosis is zygomycosis; a method for determining whether or not the mycosis is mucormycosis; a method for determining whether or not the mycosis is entomophthoramycosis; or a method for quantitatively determining the number of zygomycota cells or the degree of development of zygomycosis.

3. Reagent Kit of the Present Invention

The reagent kit of the present invention is a reagent kit for measuring zygomycota including at least one of a reagent containing an acid component and a reagent for detecting a component of zygomycota. One embodiment of the reagent kit of the present invention is a diagnosis kit for zygomycosis. Another embodiment of the reagent kit of the present invention is a diagnosis kit for mucormycosis or entomophthoramycosis.

In addition to the above reagents, the reagent kit of the present invention may further include any additional component. As described above, the additional component may be appropriately chosen in accordance with the mode of measurement of zygomycota. Examples of the additional component include a reagent for labeling or measuring a reagent for detecting a component of zygomycota, a buffer, a neutralizing agent, a standard substance, a microplate, an antigen to be immobilized on the plate, a blocking agent, a blood collection tube, and a package insert showing product information. An Example of the reagent for detecting a component of zygomycota includes an anti-chitosan antibody. An Example of the standard substance and the antigen to be immobilized on a plate includes chitosan.

In the reagent kit of the present invention, each of components may be included separately or as any combination thereof. For example, a blood collection tube containing the acid component or the reagent containing the acid component may be included in the reagent kit of the present invention. The reagent for detecting a component of zygomycota or the antigen to be immobilized on a plate may be included as a mixture with a buffer. Alternatively, the reagent or the antigen may be included in an immobilized form on a microplate.

By use of the reagent kit of the present invention, zygomycota contained in a specimen can be measured at high sensitivity through a simple procedure.

EXAMPLES

The present invention will next be described in detail by way of examples, which should not be construed as limiting the technical scope of the present invention.

In the Examples of the present invention, ELISA was performed by use of a 96-well microplate (hereinafter referred to simply as a "plate"). The used plate was F96 MaxiSorp Nunc-Immuno Plate (product of Nunc).

<Referential Example 1> Production of Anti-Chitosan Polyclonal Antibody (1) Preparation of Immunoantigen (Preparation of Chitosan-Bovine Serum Albumin Complex)

An animal is immunized with an antigen by use of a complex of chitosan hexamer (CTS6) covalently bound with bovine serum albumin (BSA) (hereinafter referred to as "CTS6-BSA"). CTS6-BSA was prepared through the following procedures.

CTS6 (product of Seikagaku Corporation) was dissolved in 0.1 M PBS (pH: 7.2) to a concentration of 20 mg/mL, and the resultant solution (4 mL) was stirred for 30 minutes. Subsequently, an EMCS solution (prepared by adding N-[6-maleimidocaproyloxy]succinimide ester (EMCS, product of Pierce) (10.4 mg) to N,N-dimethylformamide (DMF) (0.1 mL)) was added thereto, and the mixture was stirred for 1 hour, to thereby prepare CTS6 having a maleimido group (hereinafter referred to as "CTS6-MAL"). The solution was applied to a gel filtration column (PD-10 Desalting Column, product of GE Healthcare), and the eluate was recovered as fractions each having a volume of 0.5 mL. As a mobile phase, 0.1 M phosphate buffer (pH: 6.0) was used. The elution fractions of CTS6-MAL were confirmed on the basis of absorbance at 280 nm. Thus, CTS6-MAL (total volume: 3 mL) was recovered.

SPDP solution (prepared by adding N-succinimidyl-3-(2-pyridyldithio) propionate (SPDP, product of Pierce) (10 mg) to DMF (0.18 mL)) was added to a solution (5 mL) of BSA (product of Armour Pharmaceuticals) in 0.1 M PBS (pH: 6.0) having a concentration of 10 mg/mL, and the mixture was stirred for 1 hour. To the mixture were sequentially added 0.1 M Tris-HCl (pH: 7.0) (2 mL), 0.1 M ethylenediamine tetraacetic acid (EDTA) (pH: 7.0) (0.4 mL), and 1 M hydroxylamine hydrochloride (pH: 7.0) (4 mL), and the resultant mixture was stirred for 4 minutes, to thereby prepare BSA having a thiol group (hereinafter referred to as "BSA-SH"). The solution was applied to a gel filtration column (PD-10 Desalting Column), and the eluate was recovered as fractions each having a volume of 0.5 mL. As a mobile phase, 5 mM EDTA/0.1 M phosphate buffer (pH: 6.0) was used. The elution fractions of BSA-SH were confirmed on the basis of absorbance at 280 nm. Thus, BSA-SH (total volume: 6 mL) was recovered.

The above-prepared BSA-SH solution (6 mL) was concentrated through ultrafiltration (by means of Centricon 30, product of Merck KGaA) to a volume of 3 mL, and the above-prepared CTS6-MAL solution (3 mL) was added thereto. The resultant mixture was stirred overnight at 4° C., to thereby prepare CTS6-BSA. The solution was applied to a gel filtration column (PD-10 Desalting Column), and the eluate was recovered as fractions each having a volume of 0.5 mL. As a mobile phase, 0.1 M PBS (pH: 7.2) was used. The elution fractions of CTS6-BSA were confirmed on the basis of absorbance at 280 nm. The above-prepared CTS6-BSA solution was concentrated through ultrafiltration (by means of Centricon 30, product of Merck KGaA) to a total volume of 1.3 mL (concentration: 20 mg/mL), and the concentrate was used in the following tests.

(2) Preparation of Anti-Chitosan Polyclonal Antibody

An anti-chitosan polyclonal antibody (CTSpAb) was prepared through immunizing fowls with CTS6-BSA. CTSpAb was prepared through the following procedures.

To the CTS6-BSA solution (20 mg/mL, 0.015 mL), 0.1 M PBS (pH: 7.2) (0.485 mL) was added, to thereby prepare a suspension. Then, complete Freund's adjuvant (product of Sigma-Aldrich) (0.5 mL) was added to the suspension, to thereby prepare an emulsion. The entirety of the emulsion was intraperitoneally administered to each fowl (Shaver poultry, age of 2.5 months) for primary immunization. Four weeks after the first immunization, the emulsion prepared in the same manner was intraperitoneally administered again to the fowls for secondary immunization. In order to check a rise in antibody titer, blood was collected from the fowls every one week after the first immunization, and the serum antibody titer with respect to chitosan was assessed through ELISA mentioned in <Referential Example 2>. To each of the fowls exhibiting a rise in serum antibody titer, a suspension of the CTS6-BSA solution (20 mg/mL, 0.015 mL) with 0.1 M PBS (pH: 7.2) (0.485 mL) was intravenously administered for tertiary immunization.

Twelve weeks after the first immunization (i.e., 3 weeks after the tertiary immunization), the whole blood was collected from each fowl and centrifuged. The serum obtained from the supernatant was employed as "anti-chitosan polyclonal antibody (CTSpAb)" in the following tests.

<Referential Example 2> Chitosan Assay Through ELIZA by Use of Anti-Chitosan Polyclonal Antibody (1) Assay by Binding Method Binding specificity of CTSpAb to CTS was checked through a binding method. As an antigen immobilized on a plate, chitosan (CTS, product of Seikagaku Corporation, deacetylation degree: ≥80%), glycol chitosan (GCTS, product of MP Biomedicals, deacetylation degree: 76.2%), or ethylene glycol chitin (EGCTN, product of Seikagaku Corporation) was used.

To each antigen, 1% (v/v) acetic acid was added so as to adjust the concentration to 2 μg/mL. The thus-prepared solution was added to a plate at 50 μL/well, and the plate was allowed to stand overnight at 4° C. The plate was washed twice with 9.57 mM PBS (pH: 7.5) at 300 μL/well, and then 25% Block Ace (BA, product of DS Pharma Biomedical)/ 9.57 mM PBS (pH: 7.5) was added thereto at 200 µL/well. The plate was allowed to stand for 1 hour, to thereby fabricate an antigen-immobilized plate. The plate was washed repeatedly four times with 0.05% Tween-20/9.57 mM PBS (pH: 7.5) (hereinafter referred to as "PBS-T") at 300 µL/well. Then, CTSpAb diluted 16,000-fold with 10% BA/PBS-T was added to the plate at 100 µL/well, and the plate was allowed to stand for 1 hour. The plate was washed repeatedly four times with PBS-T at 300 µL/well. Subsequently, a product of peroxidase-labeled anti-fowl IgY (IgG) (H+L) antibody (product of KPL) 5,000-fold diluted with 10% BA/PBS-T was added to the plate at 100 µL/well, and the plate was allowed to stand for 1 hour. The plate was washed repeatedly four times with PBS-T at 300 µL/well, and then, SureBlue Reserve TMB Microwell Peroxidase Substrate (hereinafter referred to as "TMB reagent," product of KPL) was added to the plate at 100 µL/well, and the plate was allowed to stand for 30 minutes. Then, 1 N HCl was added to the plate at 100 µL/well. The absorbance of each well of the plate was measured by means of a well reader MP-96 (product of Seikagaku Corporation) at a measurement wavelength of 450 nm and a reference wavelength of 630 nm. Table 1 shows the results.

TABLE 1

| Antigen used in immobilization | Absorbance | |
|---|---|---|
| | Serum before immunization | Serum after immunization |
| CTS | 0.15 | 2.99 |
| GCTS | 0.13 | 2.07 |
| EGCTN | 0.11 | 0.11 |
| 10% BA/PBS-T | 0.07 | 0.20 |

As is clear from Table 1, a chitosan-immunized fowl serum (CTSpAb) exhibited the highest response to CTS. CTSpAb also exhibited reactivity with GCTS but no reactivity with EGCTN. Thus, the anti-chitosan polyclonal antibody (CTSpAb) exhibited no reactivity with chitin but particularly high specificity to chitosan.

(2) Assay by Competitive Method

Binding specificity of CTSpAb to CTS was checked through a competitive method. As a competitive substance, CTS, GCTS, or EGCTN were used.

To CTS, 1% (v/v) acetic acid was added so as to adjust the concentration to 2 µg/mL. The thus-prepared solution was added to a plate at 50 µL/well, and the plate was allowed to stand overnight at 4° C. The plate was washed twice with 9.57 mM PBS (pH: 7.5) at 300 µL/well, and then 25% BA/9.57 mM PBS (pH: 7.5) was added thereto at 200 µL/well. The plate was allowed to stand for 1 hour, to thereby fabricate CTS-immobilized plate. The plate was washed repeatedly four times with PBS-T at 300 µL/well. A solution prepared by adding 10% BA/PBS-T to the competitive substance so as to adjust the concentration to 0.01 to 10 µg/mL or 10% BA/PBS-T (competitive substance-free) was added to the plate at 100 µL/well. Then, CTSpAb diluted 16,000-fold with 10% BA/PBS-T was added to the plate at 100 µL/well, and the plate was allowed to stand for 1 hour. The plate was washed repeatedly four times with PBS-T at 300 µL/well. Subsequently, a product of peroxidase-labeled anti-fowl IgY (IgG) (H+L) antibody 5,000-fold diluted with 10% BA/PBS-T was added to the plate at 100 µL/well, and the plate was allowed to stand for 1 hour. The plate was washed repeatedly four times with PBS-T at 300 µL/well, and then, TMB reagent was added to the plate at 100 µL/well, and the plate was allowed to stand for 30 minutes. Then, 1 N HCl was added to the plate at 100 µL/well. The absorbance of each well of the plate was measured by means of a well reader MP-96 at a measurement wavelength of 450 nm and a reference wavelength of 630 nm. Table 2 shows the results.

TABLE 2

| Concn. | % Inhibition | | |
|---|---|---|---|
| (µg/mL) | CTS | GCTS | EGCTN |
| 0.01 | 1.8% | 28.1% | 0.0% |
| 0.1 | 34.8% | 62.5% | 6.0% |
| 1 | 70.4% | 82.6% | 1.3% |
| 10 | 82.5% | 84.9% | 0.0% |

Table 2 shows reduction ratios of absorbance (with competitive substance) to absorbance (free of competitive substance), as percent inhibition values. As is clear from Table 2, binding of CTSpAb to CTS on the plate was inhibited by CTS or GCTS, but was not inhibited by EGCTN. Thus, also through the competitive method, the anti-chitosan polyclonal antibody (CTSpAb) exhibited no reactivity with chitin but particularly high specificity to chitosan.

<Referential Example 3> Molecular Size of Chitosan Oligosaccharide to which Anti-Chitosan Polyclonal Antibody Bound The Molecular Size of CTS which can be assayed by CTSpAb was determined through a competitive ELISA employing a 3-mer to 6-mer CTS oligosaccharide (product of Seikagaku Corporation) as a competitive substance.

To CTS, 1% (v/v) acetic acid was added so as to adjust the concentration to 2 µg/mL. The thus-prepared solution was added to a plate at 50 µL/well, and the plate was allowed to stand overnight at 4° C. The plate was washed twice with 9.57 mM PBS (pH: 7.5) at 300 µL/well, and then 25% BA/9.57 mM PBS (pH: 7.5) was added thereto at 200 µL/well. The plate was allowed to stand for 1 hour, to thereby fabricate CTS-immobilized plate. The plate was washed repeatedly four times with PBS-T at 300 µL/well. To the plate, a solution prepared by adding 10% BA/PBS-T to the CTS oligosaccharide so as to adjust the concentration to 0.00064 to 10 µg/mL, or 10% BA/PBS-T (CTS oligosaccharide-free) was added to the plate at 100 µL/well. Then, CTSpAb diluted 8,000-fold with 10% BA/PBS-T was added to the plate at 100 µL/well, and the plate was allowed to stand for 1 hour. The plate was washed repeatedly four times with PBS-T at 300 µL/well. Subsequently, a product of peroxidase-labeled anti-fowl IgY (IgG) (H+L) antibody 5,000-fold diluted with 10% BA/PBS-T was added to the plate at 100 µL/well, and the plate was allowed to stand for 1 hour. The plate was washed repeatedly four times with PBS-T at 300 µL/well, and then, TMB reagent was added to the plate at 100 µL/well, and the plate was allowed to stand for 30 minutes. Then, 1 N HCl was added to the plate at 100 µL/well. The absorbance of each well of the plate was measured by means of a well reader MP-96 at a measurement wavelength of 450 nm and a reference wavelength of 630 nm. Table 3 shows the results.

TABLE 3

| CTS oligosacchairde | % Inhibition | | | |
|---|---|---|---|---|
| (μg/mL) | 3-mer | 4-mer | 5-mer | 6-mer |
| 0.00064 | 6% | 8% | 28% | 25% |
| 0.0032 | 9% | 15% | 42% | 39% |
| 0.016 | 11% | 23% | 55% | 51% |
| 0.08 | 16% | 34% | 65% | 63% |
| 0.4 | 24% | 45% | 69% | 66% |
| 2 | 32% | 54% | 70% | 68% |
| 10 | 44% | 63% | 70% | 68% |

Table 3 shows reduction ratios of absorbance (with CTS oligosaccharide) to absorbance (free of CTS oligosaccharide), as percent inhibition values. As is clear from Table 3, binding of CTSpAb to CTS on the plate was inhibited by 3- to 6-mer CTS oligosaccharide. Thus, through the ELISA technique employing the anti-chitosan polyclonal antibody (CTSpAb), assay of a chitosan having a molecular size of 3-mer or longer was found to be possible.

<Referential Example 4> Production of Anti-Chitosan Monoclonal Antibody

An anit-chitosan monoclonal antibody (CTSmAb) was produced through a method in reference with a document (WO 2011/049082). Specifically, CTSmAb was prepared through the following procedures.
(1) Production of Phage Antibody Library A phage antibody library was produced through a method disclosed in a document (Nakamura et al., J. Vet. Med. Sci. 2004, July; 66(7): 807-14).

An RNA fragment was extracted from isolated lymphocytes recovered from the spleen of each fowl which had undergone whole blood collection in <Referential Example 1>, and a cDNA was synthesized using the thus-obtained RNA fragment. Subsequently, each gene sequence encoding variable regions of the heavy chain and light chain of the antibody were amplified through PCR. Subsequently, a linked sequence comprising the gene sequence encoding the heavy chain and the gene sequence encoding the light chain was cloned into an expression vector (i.e., a phagemid vector) of a single strand antibody (a single chain variable fragment, scFv). Thus-obtained vector was packaged into phage particles. Then, E. coli was infected with the phage particles, whereby an amplified product was yielded. Thus, a phage antibody library was produced.
(2) Selection of Phage Antibody Through Screening A phage antibody binding to CTS was selected through panning and screening by use of a CTS-immobilized plate.

The phage antibody library obtained (1) above was added to the CTS-immobilized plate. The plate was the washed, and phages bound to CTS were recovered from E. coli. E. coli. was infected again with the phages, to thereby amplify the phages. The thus-obtained phage antibody library after panning was subjected to binding ELISA employing CTS as an immobilized sample. The absorbance was measured by use of peroxidase-labeled anti-mouse IgG (H+L) antibody (product of KPL) as a secondary antibody.

The above operations were repeated until a significant increase in absorbance was observed.

The thus-obtained phage was cloned and subjected to ELISA employing GCTS or EGCTN as an immobilized sample, whereby a clone of a phage which can bind specifically to CTS (i.e., a phage which can bind to CTS and GCTS but cannot bind to EGCTN) was yielded.

(3) Preparation of Anti-Chitosan Monoclonal IgY Antibody

An anti-chitosan monoclonal IgY antibody was prepared through a technique disclosed in a document (Shimamoto et al., Biologicals. 2005 September; 33(3): 169-74).

Gene sequences encoding variable regions of the heavy chain and light chain of the antibody were amplified through PCR employing, as a template, a clone of a phage encoding the antibody obtained in (2) above which antibody can bind specifically to CTS. Subsequently, these gene sequences were cloned into an IgY expression vector. Then, HEK293 cells transfected with the expression vector were cultured, and the culture liquid was purified, to thereby yield a monoclonal antibody (CTSmAb) which recognizes the same epitope as that recognized by the polyclonal antibody (CTSpAb) obtained in <Referential Example 1>.

<Referential Example 5> Production of HRP-Labeled Anti-Chitosan Monoclonal Antibody As a detection antibody employed in ELISA, CTSmAb labeled with horseradish peroxidase (HRP) (HRP-labeled CTSmAb) was used. HRP-labeled CTSmAb was prepared by means of Peroxidase Labeling Kit-$NH_2$ (product of Dojindo). The HRP-labeled CTSmAb was prepared through the following procedures.

Specifically, a washing buffer (100 μL) and CTSmAb (3.7 mg/mL) (54 μL) were sequentially added to a filtration tube, and the agitated mixture was centrifuged at 8,000×g for 10 minutes. Subsequently, the washing buffer (100 μL) was added again to the filtration tube, and the mixture was centrifuged again at 8,000×g for 10 minutes.

Then, an HRP-labeled solution (prepared by dissolving $NH_2$-reactive peroxidase (10 μL) in reaction buffer) was added to the filtration tube, and the mixture was allowed to stand at 37° C. for 2 hours. Thereafter, the washing buffer (100 μL) was added again to the filtration tube, and the mixture was centrifuged at 8,000×g for 15 minutes. Next, a stock solution (5% BA/9.57 mM PBS (pH: 7.5)/0.1% Pro-Clin 950) (200 μL) was added to the filtration tube, and the entirety of the mixture was recovered, to thereby yield an HRP-labeled CTSmAb.

<Referential Example 6> Preparation of Cell Body

In some Examples of the present application, a specimen containing a cell body prepared though culturing (hereinafter referred to as "cultured cell body") were subjected to measurement of zygomycota. In the Examples of the present application, the term "cell body" collectively refers to a microbe including a fungus cell and a bacterial cell. Table 4 shows the cell body employed in preparation of cultured cell bodies.

TABLE 4

| | Cell body | Culture collection No. |
|---|---|---|
| Gram-neg. | Escherichia coli DH5α | — |
| Gram-pos. | Staphylococcus aureus | ATCC25923 |
| Fungi other than zygomycota) | Aspergillus fumigatus | TIMM3968 |
| | Candida albicans | TIMM1768 |
| | Cryptococcus neoformans | TIMM0362 |
| | Trichosporon asahii | JCM2466 |

TABLE 4-continued

| | Cell body | Culture collection No. |
|---|---|---|
| Zygomycota | Absidia corymbifera | TIMM0002 |
| | Absidia corymbifera | TIMM3796 |
| | Absidia corymbifera | JCM5602 |
| | Basidiobolus ranarum | NBRC105655 |
| | Cunninghamella bertholletiae | TIMM3392 |
| | Cunninghamella echinulata | NBRC6334 |
| | Mucor circinelloides | TIMM1324 |
| | Mucor circinelloides | TIMM3176 |
| | Mucor plumbeus | TIMM1322 |
| | Mucor plumbeus | TIMM1323 |
| | Mucor racemosus | TIMM1320 |
| | Rhizomucor pusillus | TIMM6207 |
| | Rhizopus oryzae | IFM62923 |
| | Rhizopus oryzae | TIMM1327 |
| | Rhizopus oryzae | TIMM3181 |
| | Rhizopus stolonifer | TIMM1328 |
| | Rhizopus stolonifer | TIMM1329 |

Among the fungi and bacteria shown in Table 4, *Escherichia coli* DH5α was obtained from Takara Bio, and the other cell bodies were obtained from American Type Culture Collection (ATCC), Japan Collection of Microorganisms (JCM), Teikyo University Institute of Medical Mycology (TIMM), or National Institute of Technology and Evaluation (NITE) Biological Resource Center (NBRC).

The cell bodies of each of fungi and bacteria shown in Table 4 were inoculated to a RPMI1640 medium (product of Gibco) (10 mL), and the resultant medium was shake-cultured for 20 to 44 hours. The culturing temperature was set to 37° C. for bacteria and set to room temperature for fungi. Culturing was terminated when the proliferation curve exhibited a stationary phase. The medium was removed from the thus-obtained culture, to thereby recover the target cell bodies.

The above-recovered cell bodies were washed by suspending the cells in a wash liquid (physiological saline (product of Otsuka Pharmaceutical Co., Ltd.)), and the wash liquid was removed, to thereby recover the cell bodies again. These operations were repeated twice.

Among the washed cell bodies, those of each bacterium (Gram-negative and Gram-positive) were suspended in distilled water (product of Otsuka Pharmaceutical Co., Ltd.) (1 mL), to thereby prepare a suspension of cultured cell bodies. The thus-obtained suspension of cultured cell bodies was used as "cultured cell body suspension" in the following tests.

Next, the cultured cell body suspension was 10-fold diluted with distilled water, and this operation of dilution was repeated until the absorbance of the dilution reached the blank value (i.e., absorbance of distilled water), to thereby prepare a dilution of the cultured cell body suspension. The thus-obtained dilution of the cultured cell body suspension was used as a "cultured cell body specimen" in the following tests.

Also, among the washed cell bodies, those of each fungus (including zygomycota) in a state of aggregate obtained by culture were used as a "cultured cell body specimen" in the following tests.

<Referential Example 7> Preparation of Inactivated Cell Body

In some Examples of the present application, cultured cell bodies inactivated through high-pressure steam sterilization (hereinafter referred to as "inactivated cell body") were used for the purpose of ensuring operational safety. The inactivated cell bodies were prepared through the following procedures.

Among the specimens obtained in <Referential Example 6>, a cultured cell body suspension (in the case of bacteria) or a cultured cell body specimen (in the case of fungi) was subjected to high-pressure steam sterilization (121° C., 15 minutes), to thereby inactivate the cell bodies. Next, in order to remove aggregates formed from a part of cell bodies by high-pressure steam sterilization, the aggregates were precipitated through centrifugation at low speed. Subsequently, a cell body suspension was recovered from the supernatant. Since the aggregates may physically inhibit antigen-antibody reaction in ELISA, the aggregate-removed solution (supernatant of cell body suspension) was used in the following tests. The thus-obtained cell body suspension after inactivation was used as "inactivated cell body suspension" in the following tests.

Next, the inactivated cell body suspension was 10-fold diluted with distilled water, and this operation of dilution was repeated until the absorbance of the dilution reached the blank value (i.e., absorbance of distilled water), to thereby prepare a dilution of the inactivated cell body suspension. The thus-obtained dilution of the inactivated cell body suspension was used as an "inactivated cell body specimen" in the following tests.

<Referential Example 8> Calibration Curves

CTS-containing human sera and CTS-containing rabbit sera were prepared through the following procedures.

Acetic acid (1% (v/v)) was added to CTS, to thereby prepare a solution having a concentration of 62.5 ng/mL. An equivolume of acetic acid (1% (v/v)) was added to the thus-prepared solution, and this operation was repeated, whereby CTS dilutions of 62.5 to 3.9 ng/mL were prepared. A human serum or a rabbit serum (45 µL) was added to the CTS dilutions (each 5 µL), to thereby prepare standard samples having a CTS concentration of 6.25 to 0.39 ng/mL. Each standard sample was mixed with 0.2 M Tris-HCl (pH: 8.0) (450 µL), and the prepared mixtures were used in the following tests.

CTS assay was performed through sandwich ELISA. The procedures of the assay are as follows.

CTSmAb was diluted with 9.57 mM PBS (pH: 7.5) so as to adjust the concentration to 200 ng/mL. The thus-prepared solution was added to a plate at 100 µL/well, and the plate was allowed to stand overnight at 4° C. The plate was washed twice with 9.57 mM PBS (pH: 7.5) at 300 µL/well, and then 25% BA/9.57 mM PBS (pH: 7.5) was added thereto at 300 µL/well. The plate was allowed to stand for 2 hours, to thereby fabricate CTSmAb-immobilized plate. The plate was washed repeatedly four times with PBS-T at 300 µL/well. A specimen (CTS-containing human serum or CTS-containing rabbit serum) was added to the plate at 100 µL/well, and the plate was allowed to stand for 1 hour. The plate was further washed repeatedly four times with PBS-T at 300 µL/well. Subsequently, HRP-labeled CTSmAb 80,000-fold diluted with 10% BA/PBS-T was added to the plate at 100 µL/well, and the plate was allowed to stand for 1 hour. The plate was further washed repeatedly four times with PBS-T at 300 µL/well, and then, TMB reagent was added to the plate at 100 µL/well, and the plate was allowed to stand for 30 minutes. Then, 1 N HCl was added to the plate at 100 µL/well. The absorbance of each well of the plate was measured by means of a well reader MP-96 at a measurement wavelength of 450 nm and a reference wavelength of 630 nm. The measurement was performed while the plate was maintained at 37° C. by heating.

Table 5 shows the results.

TABLE 5

| CTS Concn. | Absorbance | |
|---|---|---|
| (ng/mL) | Human serum | Rabbit serum |
| 0.39 | 0.05 | 0.05 |
| 0.78 | 0.10 | 0.10 |
| 1.56 | 0.25 | 0.26 |
| 3.13 | 0.49 | 0.50 |
| 6.25 | 0.92 | 0.92 |

As is clear from Table 5, a CTS-containing rabbit serum exhibited an absorbance almost equivalent to that of a CTS-containing human serum at a common given chitosan concentration. A rabbit serum is more readily available as compared with a human serum, and has lower risk for infection with a virus or the like. Therefore, rabbit sera can be preferably used for drawing a calibration curve. In the following tests, in some Examples, a calibration curve was drawn using rabbit sera.

<Example 1> Zygomycota Measurement of Human Sera Infected with Mycosis or the Like In some Examples of the present application, human sera infected with mycosis or the like were subjected, as specimens, to measurement of zygomycota. The specimens were provided from Teikyo University Institute of Medical Mycology (TIMM).

Sera collected from human subjects infected with mycosis or the like were subjected to measurement (assay) of zygomycota. The measurement of zygomycota was performed through competitive ELIZA employing CTSpAb. The results of measurement were compared within specimens with and without performing an acid treatment.

Competitive substances (measuring targets) were prepared through the following procedures.

(a) Human Serum (without an Acid Treatment):

To a human serum (0.025 mL), 10% BA/PBS-T (0.225 mL) was added, to thereby prepare a measuring target.

(b) Human Serum (with an Acid Treatment):

2% (v/v) acetic acid (0.022 mL) was added to a human serum (0.022 mL), so as to adjust the final concentration to 1% (175 mM). The resultant mixture was stirred for 30 seconds. Subsequently, 10% BA/PBS-T (0.176 mL) was further added to the mixture, to thereby prepare a measuring target. Just after addition of acetic acid, the human serum exhibited a pH of 4.1. The pH became 4.9 after addition of 10% BA/PBS-T.

1% (v/v) acetic acid was added to CTS, so as to adjust the concentration to 2 μg/mL. The thus-prepared solution was added to a plate at 50 μL/well, and the plate was allowed to stand overnight at 4° C. The plate was washed twice with 9.57 mM PBS (pH: 7.5) at 300 μL/well, and then 25% BA/9.57 mM PBS (pH: 7.5) was added thereto at 200 μL/well. The plate was allowed to stand for 1 hour, to thereby fabricate CTS-immobilized plate. The plate was washed repeatedly four times with PBS-T at 300 μL/well. Subsequently, a mixture of CTSpAb with competitive substance (a) or (b) (prepared by mixing CTSpAb 16,000-fold diluted with 10% BA/PBS-T and equivolume of the competitive substance, and allowing the mixture to stand at 4° C. for 21 hours) was added to the plate at 100 μL/well, and the plate was allowed to stand for 1 hour. The plate was further washed repeatedly four times with PBS-T at 300 μL/well. Subsequently, a product of peroxidase-labeled anti-fowl IgY (IgG) (H+L) antibody 5,000-fold diluted with 10% BA/PBS-T was added to the plate at 100 μL/well, and the plate was allowed to stand for 1 hour. The plate was further washed repeatedly four times with PBS-T at 300 μL/well, and then, TMB reagent was added to the plate at 100 μL/well, and the plate was allowed to stand for 30 minutes. Then, 1 N HCl was added to the plate at 100 μL/well. The absorbance of each well of the plate was measured by means of a well reader MP-96 at a measurement wavelength of 450 nm and a reference wavelength of 630 nm. The measurement was performed while the plate was maintained at 37° C. by heating.

FIG. 1 and Table 6 show the measurement results.

TABLE 6

| | | Percent inhibition (%) | |
|---|---|---|---|
| Specimen No. | Diagnosed as | Non-acid treated | Acid-treated |
| 1 | Mucormycosis (rhinocerebral) | 0.1% | 30% |
| 2 | Mucormycosis (rhinocerebral) | 0.0% | 38% |
| 3 | Mucormycosis (systemic) | 0.0% | 60% |
| 4 | Mucormycosis (systemic) | 0.0% | 74% |
| 5 | *Candida tropicalis* sepsis | 0.0% | 5% |
| 6 | MRSA sepsis | 0.0% | 10% |
| 7 | *Candida albicans* sepsis | 0.0% | 4% |
| 8 | *Staphylococcus hominis* sepsis | 0.0% | 4% |
| 9 | Fungus neg. (healthy subject) | 0.0% | 9% |

Table 6 gives percent inhibition values, each being a percent reduction ratio of the absorbance in use of each specimen, in comparison with that in use of a human serum (not acid-treated, product of Kohjin Bio), as a competitive substance. As shown in FIG. 1 and Table 6, when no acid treatment was performed, all human sera did not inhibit binding of CTSpAb to CTS immobilized on the plate. In contrast, when the acid treatment was performed, non-zygomycosis human sera (specimen No. 5 to 9, including a healthy human subject serum) exhibited a percent inhibition of 10% or lower, but zygomycosis human sera (specimen No. 1 to 4, derived from different human subjects) exhibited a percent inhibition of 30% or higher. Thus, these specimens were found to significantly inhibit binding of CTSpAb to CTS. Accordingly, through subjecting a serum to an acid treatment, a measurement of zygomycota contained in a specimen can be realized, and only zygomycota can be detected as a specific cell body in use of a clinical specimen.

<Example 2> Zygomycota Measurement of Human Serum (1)

Specimens containing a cell body (with acid treatment or without acid treatment), a specimen containing no cell body (a blank sample), and CTS standard liquids for establishing a calibration curve were prepared through the following procedures.

(a) Specimens Containing a Cell Body (without Acid Treatment):

An inactivated cell body specimen (25 μL) was mixed with human serum (225 μL), and 2 M Tris-HCl (pH: 8.0) (250 μL) was added to the mixture.

(b) Specimens Containing a Cell Body (with Acid Treatment):

An inactivated cell body specimen (25 μL) was mixed with human serum (225 μL), and 5% (v/v) acetic acid (62.5 μL) was added to the mixture. The resultant mixture was allowed to stand for 1 minute at room temperature, to thereby perform an acid treatment. Thereafter, the reaction was neutralized with 2 M Tris-HCl (pH: 8.0) (187.5 μL), to thereby terminate the acid treatment.

(c) Specimen Containing No Cell Body (Blank Sample):

The procedures of (b) above were repeated, except that distilled water was used instead of the inactivated cell body specimen.

(d) CTS Standard Liquid:

1% (v/v) acetic acid was added to CTS, to thereby prepare a solution having a concentration of 200 ng/mL. An equivolume of 1% (v/v) acetic acid was added to the thus-prepared solution, and this operation was repeated, whereby CTS dilutions of 200 to 25 ng/mL were prepared. A rabbit serum (225 μL) was added to the CTS dilutions (each 25 μL), to thereby prepare standard samples having a CTS concentration of 20 to 2.5 ng/mL. Each standard sample was mixed with 2 M Tris-HCl (pH: 8.0) (250 μL), and the prepared mixtures were used in the following tests.

Zygomycota measurement was performed through sandwich ELISA. The procedures of the assay are as follows.

CTSmAb was mixed with 9.57 mM PBS (pH: 7.5) so as to adjust the concentration to 0.2 μg/mL. The thus-prepared solution was added to a plate at 100 μL/well, and the plate was allowed to stand overnight at 4° C. The plate was washed twice with 9.57 mM PBS (pH: 7.5) at 300 μL/well, and then 25% BA/9.57 mM PBS (pH: 7.5) was added thereto at 300 μL/well. The plate was allowed to stand for 2 hours, to thereby fabricate CTSmAb-immobilized plate. The plate was washed repeatedly four times with PBS-T at 300 μL/well. A specimen was added to the plate at 100 μL/well, and the plate was allowed to stand for 1 hour. Subsequently, HRP-labeled CTSmAb 40,000-fold diluted with 10% BA/PBS-T was added to the plate at 100 μL/well, and the plate was allowed to stand for 1 hour. The plate was further washed repeatedly four times with PBS-T at 300 μL/well, and then, TMB reagent was added to the plate at 100 μL/well, and the plate was allowed to stand for 30 minutes. Then, 1 N HCl was added to the plate at 100 μL/well. The absorbance of each well of the plate was measured by means of a well reader MP-96 at a measurement wavelength of 450 nm and a reference wavelength of 630 nm. The measurement was performed while the plate was maintained at 37° C. by heating.

Table 7 shows the results.

TABLE 7

| Cell body | Acid | Absorbance | | | CTS Concn. |
|---|---|---|---|---|---|
| (Bacteria/fungi) | treatment | 1st | 2nd | Av. | (ng/mL) |
| Blank | | 0.251 | 0.256 | 0.254 | — |
| *Escherichia coli* DH5α | − | 0.247 | 0.220 | 0.234 | 0.0 |
| | + | 0.259 | 0.249 | 0.254 | 0.0 |
| *Mucor circinelloides* | − | 0.251 | 0.247 | 0.249 | 0.0 |
| | + | 0.324 | 0.350 | 0.337 | 5.5 |
| *Mucor plumbeus* | − | 0.230 | 0.235 | 0.233 | 0.0 |
| | + | 0.282 | 0.305 | 0.294 | 3.4 |

In Table 7, "+" denotes that the acid treatment was performed, whereas "−" denotes that no acid treatment was performed. The CTS concentration is a converted value calculated from absorbance measurements (average) with reference to the calibration curve.

As shown in Table 7, a specimen containing *Escherichia coli* (i.e., a Gram-negative bacterium) exhibited a measurement value equal to or lower than the blank value, regardless of whether the acid treatment was performed or was not performed. Specimens containing zygomycota also exhibited measurement values lower than the blank value, when no acid treatment was performed. However, when the acid treatment was performed, these specimens exhibited measurement values significantly higher than the blank value, whereby the presence of chitosan in the specimens was confirmed. That is, the presence of zygomycota was confirmed. As a result, through conducting the acid treatment on a serum, zygomycota contained in each specimen was found to be assayed, and only zygomycota was found to be detected as a specific cell body in use of specimens other than clinical specimens.

<Example 3> Zygomycota Measurement of Human Serum (2)

A specimen containing a cell body, a specimen containing no cell body, and CTS standard liquids for establishing a calibration curve were prepared through the following procedures.

(a) Specimens Containing a Cell Body (with Acid Treatment):

An inactivated cell body specimen (12.5 μL) was mixed with human serum (112.5 μL), and 5% (v/v) acetic acid (31.3 μL) was added to the mixture. The resultant mixture was allowed to stand for 1 minute at room temperature, to thereby perform an acid treatment. Thereafter, the reaction was neutralized with 0.8 M Tris-HCl (pH: 8.0) (93.7 μL), to thereby terminate the acid treatment.

(b) Specimen Containing No Cell Body (Blank Sample):

The procedures of (a) above were repeated, except that distilled water was used instead of the inactivated cell body specimen.

(c) CTS Standard Liquid:

1% (v/v) acetic acid was added to CTS, to thereby prepare a solution having a concentration of 100 ng/mL. An equivolume of 1% (v/v) acetic acid was added to the thus-prepared solution, and this operation was repeated, whereby CTS dilutions of 25 to 1.56 ng/mL were prepared. A rabbit serum (112.5 μL) was added to the CTS dilutions (each 12.5 μL), to thereby prepare standard samples having a CTS concentration of 2.5 to 0.156 ng/mL. Each standard sample was mixed with 0.8 M Tris-HCl (pH: 8.0) (250 μL), and the prepared mixtures were used in the following tests.

Zygomycota measurement was performed through sandwich ELISA. The same procedures as described in Example 2 were performed, except that the dilution factor of HRP-labeled CTSmAb was changed to 80,000. Table 8 shows the results.

TABLE 8

| Cell body | Absorbance | | | CTS Concn. |
|---|---|---|---|---|
| (Bacteria/fungi) | 1st | 2nd | Av. | (ng/mL) |
| Blank | 0.433 | 0.437 | 0.435 | — |
| *Staphylococcus aureus* | 0.387 | 0.393 | 0.390 | 0.0 |
| *Candida albicans* | 0.399 | 0.417 | 0.408 | 0.0 |
| *Aspergillus fumigatus* | 0.417 | 0.410 | 0.414 | 0.0 |

TABLE 8-continued

| Cell body | Absorbance | | | CTS Concn. |
|---|---|---|---|---|
| (Bacteria/fungi) | 1st | 2nd | Av. | (ng/mL) |
| Absidia corymbifera | 0.922 | 0.956 | 0.939 | 0.55 |
| Rhizopus oryzae | 0.895 | 0.932 | 0.914 | 0.52 |
| Mucor racemosus | 2.878 | 2.877 | 2.878 | 2.39 |

As shown in Table 8, a specimen containing *Staphylococcus aureus* (i.e., a Gram-positive bacterium) and specimens containing *Candida albicans* or *Aspergillus fumigatus* (i.e., fungi other than zygomycota) all exhibited measurement values smaller than the blank value. In contrast, specimens containing zygomycota exhibited measurement values significantly higher than the blank value, whereby the presence of chitosan in the specimens was confirmed. That is, the presence of zygomycota was confirmed. As a result, through conducting the acid treatment on a serum, zygomycota contained in each specimen was found to be assayed, and only zygomycota was found to be detected as a specific cell body in use of specimens containing zygomycota differing from those employed in Example 2 (i.e., zygomycota other than *Mucor*).

As described in Examples 2 and 3, only zygomycota was found to be specifically detected among various fungi through the acid treatment. Also, specimens containing zygomycota belonging to *Mucor* all exhibited measurement values higher than those of specimens containing other zygomycota (i.e., 1 ng/mL or higher as converted values to CTS concentration). Thus, a fungus belonging to *Mucor* was found to be particularly suitable zygomycota for a measuring target in the present invention.

As shown in Examples 2 and 3, when the assay was performed through sandwich ELISA, specimens containing a fungus other than zygomycota exhibited measurement values almost the same as or lower than (i.e., with no significant difference) the blank value (i.e., a measurement value of a specimen containing no cell body). The concentration values, as converted to chitosan concentration, were found to be zero. In contrast, as shown in Example 1, when the assay was performed through competitive ELISA, specimens containing a cell body other than zygomycota exhibited measurement values lower than the blank value (i.e., a measurement value of a specimen containing no cell body). Thus, it was found that, when the measurement values were converted to CTS concentration, the converted values were not to become zero. In this case, a specimen of a healthy human subject must also be assayed simultaneously as a negative control. Thus, in the present invention, sandwich ELISA is preferably employed as the ELISA technique from the viewpoint of convenience of measurement.

<Example 4> Type of Acid

Specimens containing a cell body, and specimens containing no cell body were prepared through the following procedures.
(a) Specimens Containing a Cell Body (with Acid Treatment):
An inactivated cell body specimen (2.5 μL) was mixed with human serum (22.5 μL), and 2% (v/v) acid (sulfuric acid, hydrochloric acid, formic acid, or phosphoric acid) or 2% (w/v) acid (citric acid) (25 μL) was added to the mixture. The resultant mixture was allowed to stand for 1 minute at room temperature, to thereby perform an acid treatment. Thereafter, the reaction was neutralized with 0.4 M Tris-HCl (pH: 8.0) (200 μL), to thereby terminate the acid treatment.
(b) Specimen Containing No Cell Body (Blank Sample):
The procedures of (a) above were repeated, except that distilled water was used instead of the inactivated cell body specimen.

Zygomycota measurement was performed through sandwich ELISA. The same procedures as described in Example 3 were performed. Table 9 shows the results.

TABLE 9

| | Cell body | Absorbance | | |
|---|---|---|---|---|
| Acid | (Bacteria/fungi) | 1st | 2nd | Av. |
| Sulfuric acid | Blank | 0.367 | 0.368 | 0.368 |
| | Candida albicans | 0.333 | 0.343 | 0.338 |
| | Aspergillus fumigatus | 0.327 | 0.358 | 0.343 |
| | Mucor racemosus | 1.878 | 1.985 | 1.932 |
| | Rhizopus oryzae | 1.936 | 1.901 | 1.919 |
| Hydrochloric acid | Blank | 0.347 | 0.357 | 0.352 |
| | Candida albicans | 0.337 | 0.336 | 0.337 |
| | Aspergillus fumigatus | 0.317 | 0.322 | 0.320 |
| | Mucor racemosus | 1.420 | 1.547 | 1.484 |
| | Rhizopus oryzae | 1.419 | 1.420 | 1.420 |
| Formic acid | Blank | 0.346 | 0.341 | 0.344 |
| | Candida albicans | 0.330 | 0.342 | 0.336 |
| | Aspergillus fumigatus | 0.328 | 0.346 | 0.337 |
| | Mucor racemosus | 1.614 | 1.708 | 1.661 |
| | Rhizopus oryzae | 1.614 | 1.598 | 1.606 |
| Citric acid | Blank | 0.349 | 0.341 | 0.345 |
| | Candida albicans | 0.329 | 0.319 | 0.324 |
| | Aspergillus fumigatus | 0.312 | 0.314 | 0.313 |
| | Mucor racemosus | 1.164 | 1.248 | 1.206 |
| | Rhizopus oryzae | 1.227 | 1.224 | 1.226 |
| Phosphoric acid | Blank | 0.336 | 0.348 | 0.342 |
| | Candida albicans | 0.320 | 0.325 | 0.323 |
| | Aspergillus fumigatus | 0.313 | 0.315 | 0.314 |
| | Mucor racemosus | 1.168 | 1.174 | 1.171 |
| | Rhizopus oryzae | 1.080 | 1.104 | 1.092 |

In Table 9, the acid concentrations at the time of acid treatment (i.e., the mole concentration of acid when the specimen was mixed with the acid (before neutralization)) were 180 mM (sulfuric acid), 120 mM (hydrochloric acid), 260 mM (formic acid), 52 mM (citric acid), and 146 mM (phosphoric acid), respectively.

As shown in Table 9, even when the acid treatment was performed with an acid other than acetic acid, specimens containing a cell body other than zygomycota exhibited measurement values lower than the blank value. In contrast, specimens containing zygomycota exhibited measurement values significantly higher than the blank value, similar to the case in which the acid treatment was performed with acetic acid. As a result, the presence of chitosan in the specimens was confirmed. That is, the presence of zygomycota could be confirmed. As described above, through subjecting a serum to the acid treatment, zygomycota was found to be measured, and only the zygomycota was found to be specifically detected as a cell body, by use of specimens subjected to the acid treatment with an acid other than acetic acid.

<Example 5> Period of Time of Acid Treatment

Specimens containing a cell body, and specimens containing no cell body were prepared through the following procedures.

(a) Specimens Containing a Cell Body (with Acid Treatment):

An inactivated cell body specimen (5 μL) was mixed with human serum (45 μL), and 2% (v/v) acetic acid (50 μL) was added to the mixture. The resultant mixture was allowed to stand for a specific time (10 minutes, 1 hour, or 2 hours) at room temperature, to thereby perform an acid treatment. Thereafter, the reaction was neutralized with 0.4 M Tris-HCl (pH: 8.0) (200 μL), to thereby terminate the acid treatment.

(b) Specimen Containing No Cell Body (Blank Sample):

The procedures of (a) above were repeated, except that distilled water was used instead of the inactivated cell body specimen.

(c) CTS Standard Liquid:

The liquid mixtures were prepared through the procedures described in Example 3.

Zygomycota measurement was performed through sandwich ELISA. The same procedures as described in Example 3 were performed. Table 10 shows the results.

TABLE 10

| Cell body | | Absorbance | | | CTS Concn. |
|---|---|---|---|---|---|
| (Bacteria/fungi) | Time | 1st | 2nd | Av. | (ng/mL) |
| Blank | | 0.388 | 0.383 | 0.386 | — |
| *Absidia corymbifera* | 10 min | 1.511 | 1.540 | 1.526 | 1.8 |
| (TIMM3796) | 1 hour | 1.544 | 1.571 | 1.558 | 1.8 |
| | 2 hours | 1.568 | 1.572 | 1.570 | 1.8 |
| *Mucor plumbeus* | 10 min | 0.634 | 0.639 | 0.637 | 1.1 |
| (TIMM1323) | 1 hour | 0.618 | 0.621 | 0.620 | 1.1 |
| | 2 hours | 0.674 | 0.669 | 0.672 | 1.2 |

As shown in Table 10, zygomycota measurement was successfully completed with respect to all specimens, regardless of the period of time of acid treatment.

<Example 6> Temperature of Acid Treatment

Specimens containing a cell body, and specimens containing no cell body were prepared through the following procedures.

(a) Specimens Containing a Cell Body (with Acid Treatment):

An inactivated cell body specimen (5 μL) was mixed with human serum (45 μL), and 2% (v/v) acetic acid (50 μL) was added to the mixture. The resultant mixture was allowed to stand for 10 minutes at a specific temperature (room temperature (25° C.), 37° C., 50° C., or 70° C.), to thereby perform an acid treatment. Thereafter, the reaction was neutralized with 0.4 M Tris-HCl (pH: 8.0) (400 μL), to thereby terminate the acid treatment.

(b) Specimen Containing No Cell Body (Blank Sample):

The procedures of (a) above were repeated, except that distilled water was used instead of the inactivated cell body specimen.

Zygomycota measurement was performed through sandwich ELISA. The same procedures as described in Example 3 were performed. Table 11 shows the results.

TABLE 11

| | Cell body | Absorbance | | |
|---|---|---|---|---|
| Temperature | (Bacteria/fungi) | 1st | 2nd | Av. |
| Room temp. | Blank | 0.313 | 0.294 | 0.304 |
| (25° C.) | *Cryptococcus neoformans* | 0.300 | 0.283 | 0.292 |

TABLE 11-continued

| | Cell body | Absorbance | | |
|---|---|---|---|---|
| Temperature | (Bacteria/fungi) | 1st | 2nd | Av. |
| | *Aspergillus fumigatus* | 0.295 | 0.308 | 0.302 |
| | *Mucor racemosus* | 1.108 | 1.073 | 1.091 |
| | *Cunninghamella echinulata* | 1.159 | 1.162 | 1.161 |
| 37° C. | Blank | 0.274 | 0.277 | 0.276 |
| | *Cryptococcus neoformans* | 0.263 | 0.260 | 0.262 |
| | *Aspergillus fumigatus* | 0.271 | 0.271 | 0.271 |
| | *Mucor racemosus* | 1.026 | 1.045 | 1.036 |
| | *Cunninghamella echinulata* | 1.127 | 1.148 | 1.138 |
| 50° C. | Blank | 0.277 | 0.271 | 0.274 |
| | *Cryptococcus neoformans* | 0.261 | 0.261 | 0.261 |
| | *Aspergillus fumigatus* | 0.269 | 0.265 | 0.267 |
| | *Mucor racemosus* | 1.068 | 1.100 | 1.084 |
| | *Cunninghamella echinulata* | 1.071 | 1.112 | 1.092 |
| 70° C. | Blank | 0.298 | 0.320 | 0.309 |
| | *Cryptococcus neoformans* | 0.285 | 0.298 | 0.292 |
| | *Aspergillus fumigatus* | 0.283 | 0.281 | 0.282 |
| | *Mucor racemosus* | 1.070 | 1.144 | 1.107 |
| | *Cunninghamella echinulata* | 1.112 | 1.121 | 1.117 |

As shown in Table 11, zygomycota measurement was successfully completed with respect to all specimens, regardless of the temperature of the acid treatment.

<Example 7> pH at Acid Treatment (1)

Specimens containing a cell body and CTS standard liquids for establishing a calibration curve were prepared through the following procedures.

(a) Specimens Containing a Cell Body (with Acid Treatment):

Human serum (0.5 mL) and distilled water (0.5 mL) were added to a cultured cell body specimen (1 mm×1 mm, *Cunninghamella bertholletiae*), and the mixture was stirred for 30 seconds. The resultant mixture was centrifuged, and the supernatant (0.9 mL) was removed. Subsequently, human serum (0.45 mL) and distilled water (0.45 mL) were added to the specimen; the mixture was stirred for 30 seconds; the resultant mixture was centrifuged; and the supernatant (0.9 mL) was removed. These operations were repeated twice. Subsequently, human serum (0.45 mL) and acetic acid (2%, 1%, 0.4%, or 0.1%) (0.45 mL) were added to the supernatant, and the mixture was stirred for 30 seconds. The resultant mixture was allowed to stand for 5 minutes at room temperature, to thereby perform an acid treatment. Thereafter, the supernatant (0.1 mL) recovered after the centrifugation was neutralized with 0.4 M Tris-HCl (pH: 8.0) (0.4 mL), to thereby terminate the acid treatment.

(b) Specimens Containing a Cell Body (without Acid Treatment):

The procedures of (a) above were repeated, except that distilled water was used instead of acetic acid.

(c) CTS Standard Liquid:

1% (v/v) acetic acid was added to CTS, to thereby prepare a solution having a concentration of 1,000 ng/mL. An equivolume of 1% (v/v) acetic acid was added to the thus-prepared solution, and this operation was repeated, whereby CTS dilutions of 1,000 to 15.625 ng/mL were prepared. A human serum (0.9 mL) was added to the CTS dilutions (each 0.1 mL), to thereby prepare standard samples having a CTS concentration of 100 to 1.5625 ng/mL. Each standard sample was mixed with 0.4 M Tris-HCl (pH: 8.0) (0.4 mL), and the prepared mixtures were used in the following tests.

Zygomycota measurement was performed through sandwich ELISA. The procedures of the assay are as follows.

CTSmAb was mixed with 9.57 mM PBS (pH: 7.5) so as to adjust the concentration to 1 μg/mL. The thus-prepared solution was added to a plate at 100 μL/well, and the plate was allowed to stand overnight at 4° C. The plate was washed twice with 9.57 mM PBS (pH: 7.5) at 300 μL/well, and then 25% BA/9.57 mM PBS (pH: 7.5) was added thereto at 300 μL/well. The plate was allowed to stand for 2 hours, to thereby fabricate CTSmAb-immobilized plate. The plate was washed repeatedly four times with PBS-T at 300 μL/well. A specimen was added to the plate at 100 μL/well, and the plate was allowed to stand for 30 minutes. Subsequently, HRP-labeled CTSmAb 80,000-fold diluted with 10% BA/PBS-T was added to the plate at 100 μL/well, and the plate was allowed to stand for 30 minutes. The plate was further washed repeatedly four times with PBS-T at 300 μL/well, and then, TMB reagent was added to the plate at 100 μL/well, and the plate was allowed to stand for 15 minutes. Then, 1 N HCl was added to the plate at 100 μL/well. The absorbance of each well of the plate was measured by means of a well reader MP-96 at a measurement wavelength of 450 nm and a reference wavelength of 630 nm. The measurement was performed while the plate was maintained at 37° C. by heating.

Table 12 shows the results.

TABLE 12

| Acetic acid concn. (final concn.) | pH at acid treatment | CTS Concn. (ng/mL) |
|---|---|---|
| 0.9% | 4.0 | 13.6 |
| 0.45% | 4.5 | 7.0 |
| 0.18% | 5.0 | 3.6 |
| 0.045% | 6.5 | 0.0 |
| 0.0% | 8.7 | 0.0 |

In Table 12, the "acetic acid concn." refers to the final acetic acid concentration when the specimen was mixed with acetic acid (at the time of acid treatment). The "pH at acid treatment" refers to the pH value of a specimen solution at the time of acid treatment.

As shown in Table 12, when the pH was 6.5 or higher, no substantial enhancement in sensitivity of zygomycota measurement by the acid treatment was observed, whereas when the pH was lower than 6.5, an enhancement in sensitivity of zygomycota measurement by the acid treatment was suggested. More specifically, when the pH was 5 or lower, an enhancement in sensitivity of zygomycota measurement by the acid treatment was confirmed.

<Example 8> pH at Acid Treatment (2)

Specimens containing a cell body and CTS standard liquids for establishing a calibration curve were prepared through the following procedures.
(a) Specimens Containing a Cell Body (with Acid Treatment):

Human serum (0.5 mL) and distilled water (0.5 mL) were added to a cultured cell body specimen (1 mm×1 mm, *Rhizopus oryzae*), and the mixture was stirred for 30 seconds. The resultant mixture was centrifuged, and the supernatant (0.9 mL) was removed. Subsequently, human serum (0.45 mL) and distilled water (0.45 mL) were added to the specimen; the mixture was stirred for 30 seconds; the resultant mixture was centrifuged; and the supernatant (0.9 mL) was removed. These operations were repeated twice. Subsequently, human serum (0.45 mL) and hydrochloric acid (0.5 N, 0.1 N, or 0.05 N) (0.45 mL) were added to the supernatant, and the mixture was stirred for 30 seconds. The resultant mixture was allowed to stand for 5 minutes at room temperature, to thereby perform an acid treatment. Thereafter, the supernatant (0.1 mL) recovered after the centrifugation was neutralized with 0.4 M Tris-HCl (pH: 8.0) (0.4 mL), to thereby terminate the acid treatment.
(b) Specimens Containing a Cell Body (without Acid Treatment):

The procedures of (a) above were repeated, except that distilled water was used instead of hydrochloric acid.
(c) CTS Standard Liquid:

The liquid mixtures were prepared through the procedures described in Example 7.

Zygomycota measurement was performed through sandwich ELISA. The same procedures as described in Example 7 were performed. Table 13 shows the results.

TABLE 13

| HCl concn. (final concn.) | pH at acid treatment | CTS Concn. (ng/mL) |
|---|---|---|
| 0.225N | 0.7 | 36.8 |
| 0.045N | 3.4 | 32.5 |
| 0.0225N | 5.2 | 7.2 |

In Table 13, the "HCl concn." refers to the final hydrochloric acid concentration when the specimen was mixed with hydrochloric acid (at the time of acid treatment). The "pH at acid treatment" refers to the pH value of a specimen solution at the time of acid treatment.

As shown in Table 13, no particular limitation was found to be imposed on the lower limit of pH at the acid treatment, and the sensitivity of zygomycota measurement was suggested to be enhanced through acid treatment at any pH of 0 or higher. Specifically, the sensitivity of zygomycota measurement was actually enhanced through acid treatment at any pH of 0.7 or higher. Also, the sensitivity of zygomycota measurement was actually enhanced through acid treatment at any pH of 5.2 or lower.

As shown in Examples 7 and 8, the pH at the acid treatment leading to enhancement in sensitivity of zygomycota measurement was preferably 0 to 6, more preferably 0.5 to 6 or 0 to 5.5, or still more preferably 0.5 to 5.5.

<Example 9> Zygomycota Measurement of Human Serum (3)

A specimen containing a cell body, a specimen containing no cell body, and CTS standard liquids for establishing a calibration curve were prepared through the following procedures.
(a) Specimens Containing a Cell Body (with Acid Treatment):

Human serum (0.5 mL) and distilled water (0.5 mL) were added to a cultured cell body specimen (1 mm×1 mm, *Cunninghamella bertholletiae* or *Basidiobolus ranarum*), and the mixture was stirred for 30 seconds. The resultant mixture was centrifuged, and the supernatant (0.9 mL) was removed. Subsequently, human serum (0.45 mL) and distilled water (0.45 mL) were added to the specimen; the mixture was stirred for 30 seconds; the resultant mixture was centrifuged; and the supernatant (0.9 mL) was removed. These operations were repeated twice. Subsequently, human serum (0.45 mL) and 2% (v/v) acetic acid (0.45 mL) were added to the supernatant, and the mixture was stirred for 30 seconds. The resultant mixture was allowed to stand for 5 minutes at room temperature, to thereby perform an acid treatment. Thereafter, the supernatant (0.1 mL) recovered after the centrifugation was neutralized with 0.4 M Tris-HCl (pH: 8.0) (0.4 mL), to thereby terminate the acid treatment.
(b) CTS Standard Liquid:
The liquid mixtures were prepared through the procedures described in Example 7.
Zygomycota measurement was performed through sandwich ELISA. The same procedures as described in Example 7 were performed. Table 14 shows the results.

TABLE 14

| Fungi | CTS Concentration (ng/mL) |
|---|---|
| *Cunninghamella bertholletiae* | 37.0 |
| *Basidiobolus ranarum* | 54.3 |

As shown in Table 14, the acid treatment was found to be also effective for zygomycota belonging to Entomophthoraceae (*Basidiobolus ranarum*) besides zygomycota belonging to Mucorales (*Cunninghamella bertholletiae*).

<Example 10> Zygomycota Measurement of Human Serum (4)

A specimen containing a cell body, and CTS standard liquids for establishing a calibration curve were prepared through the following procedures.
(a) Specimens Containing a Cell Body (with Acid Treatment):
Human serum (0.5 mL) and distilled water (0.5 mL) were added to a cultured cell body specimen (1 mm×1 mm, *Cunninghamella bertholletiae*), and the mixture was stirred for 30 seconds. The resultant mixture was centrifuged, and the supernatant (0.9 mL) was removed. Subsequently, human serum (0.45 mL) and distilled water (0.45 mL) were added to the specimen; the mixture was stirred for 30 seconds; the resultant mixture was centrifuged; and the supernatant (0.9 mL) was removed. These operations were repeated twice. Subsequently, human serum (0.45 mL) and acetic acid (specifically, 100% (v/v) acetic acid (0.01 mL), 25% (v/v) acetic acid (0.04 mL), 10% (v/v) acetic acid (0.1 mL), or 2% (v/v) acetic acid (0.45 mL)) were added to the supernatant, and the mixture was stirred for 30 seconds. The resultant mixture was allowed to stand for 5 minutes at room temperature, to thereby perform an acid treatment. Thereafter, distilled water was added to the acid-treated specimen so as to adjust the total volume to 1 mL. Subsequently, the supernatant (0.1 mL) recovered after the centrifugation was neutralized with 0.4 M Tris-HCl (pH: 8.0) (0.4 mL), to thereby terminate the acid treatment.
(b) CTS Standard Liquid:
The liquid mixtures were prepared through the procedures described in Example 7.
Zygomycota measurement was performed through sandwich ELISA. The same procedures as described in Example 7 were performed. Table 15 shows the results.

TABLE 15

| Acetic acid concn. | Additive amount | Serum concn. | pH at acid treatment | CTS Concn. (ng/mL) |
|---|---|---|---|---|
| 100% | 0.01 mL | 89% | 3.9 | 14.3 |
| 25% | 0.04 mL | 85% | 3.9 | 19.1 |
| 10% | 0.1 mL | 77% | 3.9 | 20.7 |
| 2% | 0.45 mL | 50% | 4.0 | 13.6 |

In Table 15, the "acetic acid concn." refers to the concentration of acetic acid added to the specimen for the acid treatment; the "additive amount" refers to the volume of acetic acid added to the specimen for the acid treatment; the "serum concn." refers to the concentration of human serum at the time of acid treatment; and the "pH at acid treatment" refers to a pH value of a specimen solution at the time of acid treatment.

As shown in Table 15, the presence of chitosan in a specimen was confirmed, regardless of the concentration of human serum at the time of acid treatment. That is, the presence of zygomycota in a specimen was confirmed.

Accordingly, in the present invention, a specimen (e.g., a human serum) can be subjected to the acid treatment, without performing a pretreatment of diluting a specimen with a solvent such as water.

<Example 11> Zygomycota Measurement of Human Serum (5)

A specimen containing a cell body and a specimen containing no cell body were prepared through the following procedures.
(a) Specimens Containing a Cell Body (with Acid Treatment):
An inactivated cell body specimen (*Mucor racemosus*) (8 μL) was mixed with human serum (72 μL), and 5% (v/v) acetic acid (20 μL) was added to the above-obtained mixture. The resultant mixture was allowed to stand for 5 minutes at room temperature, to thereby perform an acid treatment. Thereafter, the reaction was neutralized with 0.8 M Tris-HCl (pH: 8.0) (60 μL), to thereby terminate the acid treatment.
(b) Specimens Containing a Cell Body (without Acid treatment):
The procedures of (a) above were repeated, except that distilled water was used instead of acetic acid.
A suspension of CTSmAb-bound latex particles (i.e., CTSmAb-sensitized latex liquid) was prepared by means of a commercial kit (IMMUTEX P0307, product of JSR) according to the procedures described in the package insert. The procedures for preparation are as follows.
A polymer particle suspension for immunological diagnosis (125 μL), 20 mM MES-NaOH (pH: 6.0, 420 μL), CTSmAb (3.7 mg/mL, 25 μL) were mixed together, and the mixture was allowed to stand at room temperature for 1 hour. The resultant liquid was mixed with 1% EDC•HCl (1-ethyl-3-(3-dimethylaminopropyl)carbodiimide hydrochloride) solution (12.5 μL), and the mixture was allowed to stand at room temperature for 1 hour. The resultant liquid was centrifuged at 15,000×g for 30 minutes, and the supernatant was removed, to thereby recover polymer particles. The polymer particles were mixed with 25% Block Ace (0.5 mL), and the mixture was subjected to ultrasonication. The resultant liquid was centrifuged at 15,000×g for 30 minutes, and the polymer particles were recovered again by removing the supernatant. The thus-prepared particles were mixed with R2 Buffer (0.5 mL), and the mixture was subjected to ultrasonication. The resultant liquid was allowed to stand at room temperature for 1 hour and subjected again to ultrasonication, whereby the particles were dispersed in the liquid. Thereafter, the liquid mixture was allowed to stand at 37° C. for 20 hours. The thus-yielded liquid was employed as a "CTSmAb-sensitized latex liquid" in the following tests.

Zygomycota measurement was performed through the latex flocculation test. The procedures for measurement are as follows.

Specifically, a specimen (75 μL) was added dropwise to a section of a reaction plate (Sero-direct "Eiken" *Cryptococcus*, product of Eiken Chemical Co., Ltd.), and the specimen was spread in the section. Subsequently, the CTSmAb-sensitized latex liquid (25 μL) was added dropwise to the section. The reaction plate was shaken for 10 minutes by means of a horizontally rotating shaker, to thereby mixing the specimen and the latex liquid. The presence or absence of aggregates was visually checked.

In the above tests, the specimens with the acid treatment formed aggregates, whereas those without the acid treatment didn't form aggregates. That is, in the present invention, the zygomycota measurement was found to be accomplished through a flocculation method. Thus, those skilled in the art can readily understand that zygomycota measurement is possible through another assay technique (e.g., turbidimetry or nephelometry) employing a particle agent such as an antibody-bond latex particle agent. Also, those skilled in the art can readily understand that zygomycota measurement is realized through any assay technique by use of an antibody, other than enzyme immunoassay and flocculation technique (e.g., immuno-chromatography or immuno-blotting).

<Example 12> Zygomycota Measurement of Non-Human Serum

A specimen containing a cell body, and CTS standard liquids for establishing a calibration curve were prepared through the following procedures.

(a) Specimens Containing a Cell Body (with Acid Treatment):

A sample (plasma, a serum, or a physiological saline (0.5 mL each)) was added to a cultured cell body specimen (1 mm×1 mm, *Rhizopus oryzae* or *Cunninghamella bertholletiae*), and the mixture was stirred for 30 seconds. The sample was human plasma (product of Cosmo Bio), a horse serum (product of Cosmo Bio), a bovine serum (Nippon Biotest Laboratories Inc.), a rabbit serum (product of Kohjin Bio Co., Ltd.), or a physiological saline (product of Otsuka Pharmaceutical Co., Ltd.). The resultant mixture was centrifuged, and the supernatant (0.9 mL) was removed. Subsequently, the sample (a serum, plasma, or saline (0.45 mL each)) and distilled water (0.45 mL) were added to the specimen; the mixture was stirred for 30 seconds; the resultant mixture was centrifuged; and the supernatant (0.9 mL) was removed. These operations were repeated twice. Subsequently, the sample (a serum, plasma, or saline (0.45 mL each)) and 2% (v/v) acetic acid (0.45 mL) were added to the supernatant, and the mixture was stirred for 30 seconds. The resultant mixture was allowed to stand for 5 minutes at room temperature, to thereby perform an acid treatment. Thereafter, the supernatant (0.1 mL) recovered after the centrifugation was neutralized with 0.4 M Tris-HCl (pH: 8.0) (0.4 mL), to thereby terminate the acid treatment.

(b) CTS Standard Liquid:

The liquid mixtures were prepared through the procedures described in Example 7.

Zygomycota measurement was performed through sandwich ELISA. The same procedures as described in Example 7 were performed. Table 16 shows the results.

TABLE 16

| Specimens | Fungus | CTS Concn. (ng/mL) |
|---|---|---|
| Human plasma | *Rhizopus oryzae* | 71.9 |
| Horse serum | *Cunninghamella bertholletiae* | 89.5 |
| Bovine serum | *Cunninghamella bertholletiae* | 101.9 |
| Rabbit serum | *Cunninghamella bertholletiae* | 99.8 |
| Physiol. saline | *Cunninghamella bertholletiae* | 104.4 |

As shown in Table 16, zygomycota measurement was found to be possible for specimens other than a human serum. Particularly, it was found that zygomycota measurement was possible for a physiological saline. Thus, in the present invention, a specimen subjected to zygomycota measurement may be bronchoalveolar lavage fluid (BALF). Therefore, no particular limitation is imposed on the specimen to be assayed in the present invention, so long as the specimen is a substance which may contain zygomycota.

INDUSTRIAL APPLICABILITY

According to the present invention, zygomycota contained in a specimen can be measured at high sensitivity. Thus, the present invention may be employed as means for realizing a serological diagnosis for zygomycosis such as mucormycosis or entomophthoramycosis, the means being effective for an early diagnosis thereof.

The entirety of Japanese Patent Application No. 2015-063887 (filing date: Mar. 26, 2015) is incorporated herein by reference. All documents, specifications of patent application, and technical standards are incorporated herein by reference, in such a manner as being specifically and individually present.

The invention claimed is:

1. A method for detecting zygomycosis, the method comprising:
   adjusting pH of a specimen derived from an animal to 6 or lower by an acid treatment, and
   measuring zygomycota by measuring chitosan in the specimen by immunoassay, thereby detecting zygomycosis,
   wherein the zygomycosis is mucormycosis or entomophthoramycosis, and
   wherein the entomophthoramycosis is caused by a fungus belonging to *Basidiobolus ranarum*.

2. The method according to claim 1, wherein the acid treatment is performed by combining an untreated specimen with an acid.

3. The method according to claim 1, wherein the immunoassay is performed using an anti-chitosan antibody.

4. The method according to claim 1, wherein the animal-derived specimen is selected from the group consisting of a sputum, a cerebrospinal fluid, a nasal swab, a pharyngeal swab, a nasal aspirate, an ascites, a bronchoalveolar lavage fluid (BALE), a biopsy specimen, and a blood-derived sample.

5. The method according to claim 4, wherein the blood-derived sample is serum or plasma.

6. The method according to claim 1, wherein the specimen is a liquid specimen.

7. The method according to claim 6, wherein the liquid specimen is a liquid specimen which has been concentrated or diluted.

8. The method according to claim 6, wherein the liquid specimen is prepared by dissolving a solid specimen.

\* \* \* \* \*

UNITED STATES PATENT AND TRADEMARK OFFICE
CERTIFICATE OF CORRECTION

| | |
|---|---|
| PATENT NO. | : 10,955,413 B2 |
| APPLICATION NO. | : 15/561265 |
| DATED | : March 23, 2021 |
| INVENTOR(S) | : Maki Aizawa and Koichi Makimura |

It is certified that error appears in the above-identified patent and that said Letters Patent is hereby corrected as shown below:

On the Title Page

Item (56) right column, Line 1, delete "pathogensis," and insert therefor --pathogenesis,--.

Item (56) right column, Line 37, delete "Chuba" and insert therefor --Chubu--.

Page 2, item (56) right column, Line 10, delete "Chuba" and insert therefor --Chubu--.

In the Specification

Column 16, Line 24, delete "hydridoma" and insert therefor --hybridoma--.

Column 16, Line 25, delete "chitonsan-immunized" and insert therefor --chitosan-immunized--.

Column 16, Line 38, delete "hydridoma" and insert therefor --hybridoma--.

Column 19, Line 44, delete "N-[6-" and insert therefor --N-[ε- --.

Column 22, Line 34, delete "Molecular Size" and insert therefor --molecular size--.

Column 23, Line 2, delete "oligosacchairde" and insert therefor --oligosaccharide--.

Column 23, Line 25, delete "anit-" and insert therefor --anti- --.

Column 24, Line 64, delete "other" and insert therefor --(other--.

In the Claims

Column 40, Line 62, in Claim 4, delete "(BALE)," and insert therefor --(BALF),--.

Signed and Sealed this
Eighth Day of June, 2021

Drew Hirshfeld
*Performing the Functions and Duties of the
Under Secretary of Commerce for Intellectual Property and
Director of the United States Patent and Trademark Office*